(12) United States Patent
Gharib et al.

(10) Patent No.: US 11,839,427 B2
(45) Date of Patent: Dec. 12, 2023

(54) SYSTEMS, METHODS, AND APPARATUSES FOR OCULAR MEASUREMENTS

(71) Applicant: CALIFORNIA INSTITUTE OF TECHNOLOGY, Pasadena, CA (US)

(72) Inventors: Morteza Gharib, Altadena, CA (US); Alexei Harvard, Pasadena, CA (US); Alessio Tamborini, Pasadena, CA (US); David Jeon, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 444 days.

(21) Appl. No.: 16/846,155

(22) Filed: Apr. 10, 2020

(65) Prior Publication Data

US 2020/0323427 A1    Oct. 15, 2020

Related U.S. Application Data

(60) Provisional application No. 62/950,753, filed on Dec. 19, 2019, provisional application No. 62/833,478, filed on Apr. 12, 2019.

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/1005* (2013.01); *A61B 3/107* (2013.01);
(Continued)

(58) Field of Classification Search
CPC ... A61B 5/7282; A61B 5/7278; A61B 5/0205; A61B 3/165; A61B 3/14; A61B 3/1241; A61B 3/107; A61B 3/1005; A61B 3/0025
(Continued)

(56) References Cited

U.S. PATENT DOCUMENTS 6,229,913 B1   5/2001   Nayar et al.
6,278,847 B1   8/2001   Gharib et al.
(Continued)

FOREIGN PATENT DOCUMENTS

DE    102010010569 A1 *   9/2011   ........... A61B 3/0008
WO    WO-2013114127 A1 *   8/2013   ............... A61H 5/00
WO    WO-2018167099 A2 *   9/2018   ........... A61F 2/1635

OTHER PUBLICATIONS

WO, PCT/US20/27806 ISR and Written Opinion, dated Jul. 17, 2020.
(Continued)

*Primary Examiner* — James R Greece
(74) *Attorney, Agent, or Firm* — ONE LLP

(57) ABSTRACT

Systems, methods and apparatuses are provided for the measurement of intraocular pressure. These systems, methods and apparatuses can include an imaging apparatus for capturing two- or three-dimensional images or video of a patient's eye. An image reconstruction based on the captured images or video can be performed, and measurements can be taken of blood vessel features, curvature metrics, or distances between point pairs. In some embodiments, blood pressure measurements can also be taken synchronously with the captured images or video. From these measurements, a relationship between certain medical condition (e.g., elevated intraocular pressure, heart arrhythmia) and the extracted metrics can be established.

16 Claims, 22 Drawing Sheets

(51) Int. Cl.
*A61B 3/107* (2006.01)
*A61B 3/14* (2006.01)
*A61B 3/12* (2006.01)
*A61B 3/16* (2006.01)
*A61B 5/00* (2006.01)
*A61B 5/0205* (2006.01)

(52) U.S. Cl.
CPC .............. *A61B 3/1241* (2013.01); *A61B 3/14* (2013.01); *A61B 3/165* (2013.01); *A61B 5/0205* (2013.01); *A61B 5/7278* (2013.01); *A61B 5/7282* (2013.01); *A61B 3/0041* (2013.01); *A61B 5/0013* (2013.01)

(58) Field of Classification Search
USPC ......................................................... 600/301
See application file for complete search history.

(56) References Cited

U.S. PATENT DOCUMENTS

| | | | |
|---|---|---|---|
| 7,612,870 | B2 | 11/2009 | Graff et al. |
| 9,530,213 | B2 | 12/2016 | Gharib et al. |
| 2003/0195438 | A1* | 10/2003 | Petillo ................ A61H 23/0263 601/78 |
| 2005/0117118 | A1* | 6/2005 | Miller ...................... A61B 3/13 606/4 |
| 2006/0140454 | A1* | 6/2006 | Northcott ............... G06V 40/19 382/117 |
| 2014/0313515 | A1 | 10/2014 | Hogan |
| 2015/0320308 | A1 | 11/2015 | Akiba et al. |
| 2016/0066778 | A1 | 3/2016 | Imamura |
| 2017/0017083 | A1 | 1/2017 | Samec et al. |
| 2017/0209046 | A1 | 7/2017 | Gharib |
| 2018/0296086 | A1 | 10/2018 | Korb et al. |
| 2020/0078212 | A1* | 3/2020 | Seo .......................... A61F 7/02 |

OTHER PUBLICATIONS

Kaufmann, C., et al., "Ocular Pulse Amplitude in Healthy Subjects as Measured by Dynamic Contour Tonometry", Arch Ophthalmol., 2006, vol. 124, No. 8, pp. 1104-1108.

* cited by examiner

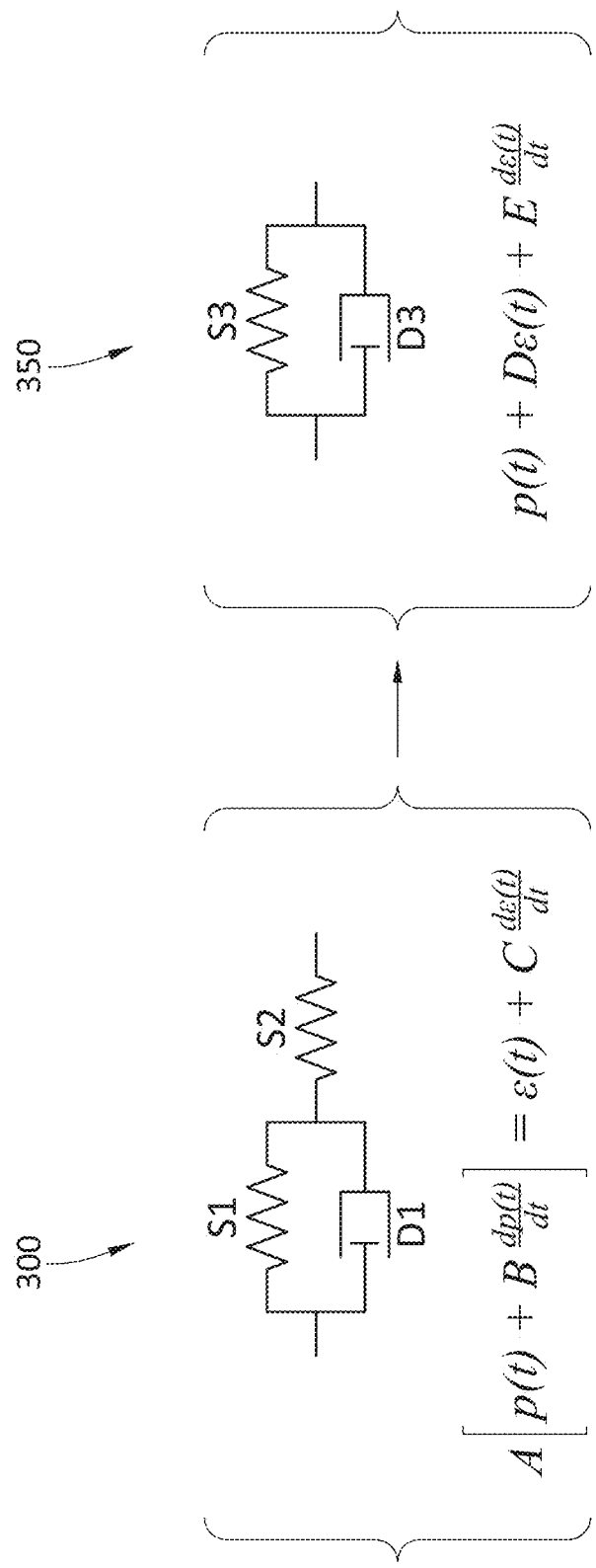

SYSTEMS, METHODS, AND APPARATUSES FOR OCULAR MEASUREMENTS

CROSS-REFERENCE TO RELATED APPLICATIONS

This application claims priority to U.S. Provisional Application Ser. No. 62/833,478, filed Apr. 12, 2019, and to U.S. Provisional Application Ser. No. 62/950,753, filed Dec. 19, 2019, both of which are hereby expressly incorporated by reference in their entireties for all purposes.

FIELD OF INVENTION

The subject matter described herein relates to systems, methods, and apparatuses for the measurement of one or more eye characteristics to enable medical diagnosis.

BACKGROUND

The eye is a complex and vital organ and it can be susceptible to many diseases such as, but not limited to, age-related macular degeneration, retinal pigment epithelial, retinal vein occlusion, and glaucoma. The eye is also connected to other bodily systems such as, but not limited to, the vascular system. Thus, it is essential that various characteristics of the eye are measured and monitored such that the onset of various diseases of the eye and heart (e.g., arrythmia) can be detected.

As an example, glaucoma is a complex disease in which the build-up of fluid in the eye causes damage to the optic nerve, afflicts approximately two million people in the United States, and many more millions globally. Left untreated, glaucoma can result in eye pain, blurred vision, nausea, and irreversible vision loss, amongst other adverse conditions. It is the second-leading cause of blindness worldwide, and the leading cause of blindness in people over sixty years old.

If diagnosed and treated early enough, however, it is possible to slow or stop the progression of glaucoma and prevent blindness. An important risk factor associated with glaucoma is an elevated intraocular pressure (IOP). In this respect, monitoring IOP is an important task that is crucial to inform patients and doctors about stages of the disease, as well as methods to be used for intervention and therapeutic approaches.

Known IOP measurement techniques are invasive and usually include direct contact with the sclera of the eye, either by touching it with an applicator or by using air jets to create local pressure. These approaches are aimed at trying to create a physical depression in the eye that can be measured and used to estimate IOP through pre-determined data for a given age and gender. These invasive approaches, especially when performed repeatedly, often require the eye to be anesthetized and may lead to undetected injuries while the eye is under anesthesia. Additionally, there are general assumptions about the sclera's geometrical and mechanical properties that may not necessarily apply to a given patient. In this respect, large variations in measuring IOP in a clinical setting using these known approaches is expected.

Accordingly, there is a present need for systems, methods, and/or apparatuses for non-invasively and more accurately measuring ocular characteristics/properties for use in the diagnosis of at least eye and vascular diseases.

SUMMARY

Described herein are example embodiments of systems, methods, and apparatuses for performing contactless measurement of one or more characteristics of a patient's eye used to diagnosis a potential medical condition. One of the systems can include: a light source configured to illuminate the eye; a 3D-camera assembly configured to capture a plurality of images of the eye; a 3D-reconstruction module configured to generate a 3D model of the eye based at least on the plurality of images; and a data analytic module configured to determine one or more characteristics of the eye based at least on the 3D model. Each of the plurality of images can have depth information.

The one or more characteristics of the eye can include one or more of blood vessel features, curvature metrics of a sclera of the eye, volumetric pulsations of the eye, total eye volume, deformations, relative local displacements over time, and radius of the eye.

The system can further include an intraocular pressure (IOP) diagnostic module configured to determine the IOP within the eye based at least on volumetric pulsations of the eye and/or a rate of change of deformation of the eye over time.

In some embodiments, the system can also include a blood pressure monitoring apparatus to synchronously measure the patient's blood pressure. In this embodiment, the IOP diagnostic module can determine the IOP within the eye based at least on the patient's blood pressure and the volumetric pulsation of the eye.

The system can also include a heart monitor configured to obtain heart data of the patient's heart and a diagnostic module configured to flag a potential medical condition based at least on (a) deformations of the eye and the heart data, (b) relative local displacements over time and heart data, OR (c) variation in the relative local displacements over time and heart data.

The diagnostic module can determine pulsatile ocular blood flow (POBF) based at least on the volumetric pulsations of the eye. The 3D-camera assembly can be a plurality of cameras in stereoscopic alignment, one or more cameras that can capture a plurality of images at different focuses, one or more off-axis cameras with Scheimpflug angles, or a telecentric camera and an off-axis camera. Each of the camera can be a high-speed camera that can capture images at a frame rate between 30-5000 frames per second. The light source can have a wavelength with a range between 350 and 450 nm to avoid the peak of the blue light hazard. In some embodiments, the light source can have a wavelength of 400 nm.

A second system for identifying potential medical conditions using contactless measurement of one or more characteristics of a patient's eye is also disclosed. The second system includes: a light source configured to illuminate the eye; a 3D-camera assembly configured to capture a plurality of images of the eye, wherein the plurality of images comprises depth information; a non-transitory memory; and one or more processors. The non-transitory memory can store instructions that, when executed by one or more processors, cause the one or more processors to: generate a 3D model of a portion of the eye based at least on the plurality of images; determine one or more characteristics of the eye based at least on the 3D model, wherein the one or more characteristics comprise one or more of blood vessel features (e.g., patterns), curvature metrics of a sclera of the eye, volumetric pulsations of the eye, total eye volume, deformations, relative local displacements over time, and radius of the eye; and identify a potential medical condition based at least on the one or more characteristics of the eye. The 3D model can contain more information than a mesh or texture such as, but not limited to, a model of multiple portions of the eye, a model of one or more blood vessels, or super-resolved representation of portions of the eye with associated probability distributions.

A method for performing contactless measurement of one or more characteristics of a patient's eye to diagnosis a potential medical condition is also disclosed. The method includes: illuminating the eye with light; capturing a plurality of images of the eye having depth information; reconstructing a stereo model of the eye based at least on the plurality of images; and determining one or more characteristics of the eye based at least on the stereo model of the eye.

The one or more characteristics of the eye can include one or more of blood vessel patterns, curvature metrics of a sclera of the eye, volumetric pulsations of the eye, total eye volume, deformations, relative local displacements over time, and radius of the eye.

The method can further include determining an intraocular pressure of the eye based at least on a volumetric pulsations of the eye, which can be the rate of change of deformation of the eye over time.

The method can also include obtaining heart data of the patient's heart and identifying a potential medical condition based at least on (a) deformations of the eye and the heart data, (b) relative local displacements over time and heart data, OR (c) variation in the relative local displacements over time and heart data.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3A and 3B illustrate simple proof of concept viscoelastic model of a human eye in accordance with example embodiments of the present disclosure.

DETAILED DESCRIPTION

Figure 1:
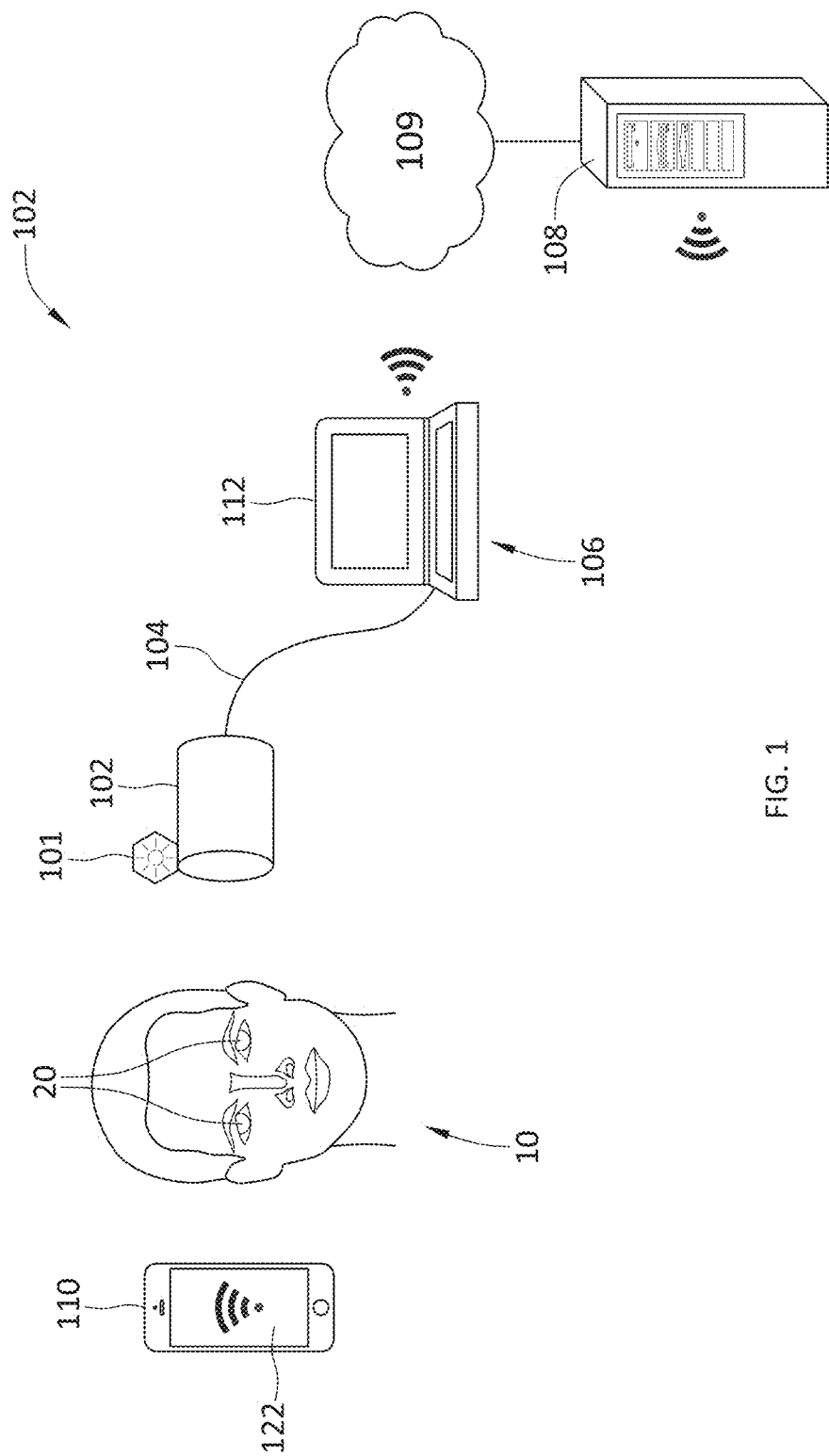
FIG. 1 is a diagrammatic overview of an example embodiment of a system for performing ocular measurements.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

Overview & Applications

Current diagnostic methodologies such as contact tonometry use a one-time measurement to diagnose a patient's eye condition. Since the tonometry is a contact procedure, its measurements are assumed to stay constant for each patient. This absolute treatment of eye measurements is wrong and can lead to incorrect diagnoses. For example, conventional methodologies are implemented to facilitate diagnostic procedures for a large groups of people. However, for many degenerative diseases, the progression of certain eye characteristics (e.g., deformation, ocular flow) over time is a more accurate parameter for monitoring and diagnosing potential eye diseases. Unfortunately, conventional methodologies are limited by their inherent invasiveness and inaccuracy. Currently, most diagnostic devices require a trained ophthalmologist to perform the procedure and have scarce repeatability even within the same visit. Accordingly, what is needed is a non-invasive (e.g., contactless), accurate, and repeatable ocular measurement method. The disclosed systems and methods for performing contactless measurement of one or more characteristics of a patient's eye allow doctors to compare measurements at different instances in time for an individual patient. In this way, a progressive understanding of the disease can be efficiently and accurately created. Since each patient's eye characteristics are unique, the ability to measure and track various eye's characteristics over time will lead to a more accurate and timely diagnosis.

The eye is a viscoelastic quasi-spherical structure with a pulsatile inflow and a constant outflow of blood. The fluctuating net flow of blood in the eye creates periodic volumetric expansions and contractions corresponding to positive and negative net flow patterns, respectively. For each cardiac cycle, the eye undergoes radial expansions and contractions that reflect the net inflow and outflow of blood from the eye, respectively. Given the incompressibility of blood, volumetric fluctuations in the eye are directly related to the quantity of blood entering the eye. Additionally, during an ocular radial expansion, the expansion of certain portion of the eye (e.g., sclera) is mainly driven by an incoming pressure wave. During an ocular radial contraction, the contraction behavior is mainly determined the by material properties of the sclera. For example, tension forces of the ocular wall can cause passive recoil that drive the blood outflow. Accordingly, the ocular properties (e.g., sclera elasticity, size) can be extracted from analysis of the shape, slope, and frequencies of the ocular pulsations, which dictate the ocular response to the incoming pressure wave.

By exploiting the observable pulsatile behavior and other attributes of the eye, the disclosed systems and methods can measure local curvature of the eye over-time and reconstruct the ocular volumetric pulsations. This allows net flow profiles in the eye to be measured. In some embodiments, high-speed imaging system, coupled with image analysis algorithms, can be employed to measure various characteristics of the eye such as, but not limited to, blood vessel patterns, curvature metrics of a sclera of the eye, total eye volume, deformations, relative local displacements over time, and radius of the eye. One or more of these characteristics can be used to generate and/or measure a 3D blood vessel model, bulk 3D shape of the eye, local and/or regional blood outflow measurements, pulse pressure waveform of the blood flow, waveform propagation, waveform variation, and time based observation of the pulse pressure waveforms, blood vessels characteristics, deformations, and physical properties of the sclera.

In some embodiments, the disclosed systems and methods can use keypoints extraction and matching (e.g., ORB, SIFT, SURF, or neural network-derived features), template matching, and/or pattern recognition to identify areas on the sclera that can be tracked by an imaging apparatus (e.g., one or more cameras) to generate one or more of the above eye characteristics over time or at an instance of time. Based at least on this information, relative IOP changes can be determined without the need for repeated invasive techniques.

The disclosed systems and methods for performing contactless measurement of one or more characteristics of the eye can also be used for non-invasive observation of the eye's pulse pressure wave. As extensively documented in the cardiovascular literature, pulse pressure waveforms carry information regarding the cardiovascular system's health. For this reason, measuring ocular radial pulsations provides a direct means of extracting pulse pressure wave shape information. For example, it has been observed that abnormalities in the measured ocular radial pulsations generally corresponds to abnormality in the pulse pressure wave. Accordingly, in some embodiments, the systems and methods can "non-contactly" (e.g., contactless) measure and use ocular properties (e.g., radial pulsation) to extract information regarding the cardiovascular system.

Additionally, an understanding of a patient's heart activity and health can be developed by analyzing the pulse pressure waveform over an extended period. A healthy heart functions with a consistent rhythmic pattern—accelerating and decelerating its pace to accommodate the body's oxygen demands. Multiple heart conditions affect this rhythmic pattern of the heart resulting in inefficient heart function and greater risks of heart failure. As the ocular radial pulsations are reflective of the cardiac activity, these can be used to directly measure the heart rhythmic patterns. Accordingly, in some embodiments, the systems and methods can non-contactly measure the ocular radial pulsations for a period of time (greater than one pulsation) to assess the heart's rhythmic function and health.

In some embodiments, the disclosed systems and methods for performing contactless measurement of one or more characteristics of the eye can be used to diagnosis or identify potential eye conditions such as, but not limited to, diabetic retinopathy, macular degeneration, or retinal vein occlusion. Take diabetic retinopathy as an example, it is a diabetes complication that affects the vasculature of the eyes. During the early stages of diabetic retinopathy, the persistence of hyperglycemia degenerates the retinal vasculature of the eye leading to hemorrhaging, aneurysms and hard exudates. As the disease progresses, the damaged eye vasculature induces the formation of new blood vessels in a process known as neovascularization. This process is rapid and unorganized, affecting the regular ocular flow regimes. Elucidating the fluid dynamics involved in this process can motivate the application of ocular blood flows measurements as an early diagnostic tool.

At the macroscopic scale, the vasculature changes in the eye affect the flow resistance directly influencing ocular blood flows. In the early stages of the disease, the ocular blood flow is reduced as hemorrhaging, aneurysms and hard exudates increase flow resistances. However, as the disease progresses, increased vasculature reduces flow resistance and thereby inducing increased flow. Additionally, pulsatile ocular blood flow (POBF), which can be an indicator of the progression of diabetic retinopathy, can be measured by measuring and tracking the amount of blood entering the eye during a given period of time (e.g., a beat, a second, a minute). Previous studies have demonstrated that the POBF increased with disease severity. Accordingly, by monitoring and tracking the ocular blood flow (e.g., POBF) using the disclosed non-invasive eye measurement technique, diabetic retinopathy can be potentially diagnosed. Further discussion of POBF measurement is provided below.

In some embodiments, the disclosed systems and methods utilize surface curvature measurements to estimate ocular blood flows. Here, fluctuating flow profiles of the eye are measured by analyzing the radial pulsatile behavior of the ocular shell. In this way, the hemodynamic behaviors and health of the eye can be directly analyzed. Since hemodynamic changes precede ocular damage, the disclosed systems and methods for measuring characteristics of the eye to measure and monitor hemodynamic behaviors can be used to identify potential ocular issues.

Another diagnostic application of the disclosed systems and method is for diagnosing age-related macular degeneration (AMD), which is a degenerative disease that damages the macular region leading to blindness. The early stages of the disease are characterized with the deposition of insoluble extracellular aggregates called drusen in the retina. During the progression of the disease, the choroid vascular density is highly reduced and choriocapillaris become vasoconstricted. AMD can progress in two distinct forms: the non-exudative and exudative AMD. Non-exudative AMD, or dry AMD, is a progression of the early stage AMD with a degeneration of the retinal pigment epithelial (RPE) layer. The late stage dry AMD, called geographic atrophy, results in large areas of degenerated RPE.

The exudative (wet) AMD is characterized by choroidal neovascularization towards the outer retina. The onset of this disease is very rapid and can lead to blindness if left untreated. Elevated choroid vascular density reduction during disease progression is believed to be one of the major factors for transition to the wet stage of AMD. Previous medical studies have analyzed the choroidal blood flow as measured with POBF during AMD disease progression. Previous studies showed that the progression of the disease was marked with a decrease in POBF, and that decreased POBF may be a risk factor for choroidal neovascularization. Accordingly, by monitoring and tracking the patient's POBF using the disclosed non-invasive eye measurement technique, AMD can be potentially diagnosed.

Another diagnostic application of the disclosed systems and method is for diagnosing Retinal Vein Occlusion (RVO), which is a medical condition where the retinal veins develop a small clot that reduces or blocks the vein outflow. When vein outflow is decreased, several conditions can develop in the eye leading to blindness if left untreated. These include macular edema, retinal neovascularization, and glaucoma. The blocked outflow from the eye causes a buildup of fluid that increases vascular resistance and decreases nutrient supply. In RVO, decreased retinal blood outflow is typically compensated with a more than proportionate increase in choroidal blood flow. This mechanism is used to maintain normal O2 oxygen levels in the retina and given the greater diffusion distance between the choroid and the inner retina greater O2 concentrations are required. Several studies have analyzed this phenomenon and concluded that POBF is indeed increased in the eye having RVO. Additionally, it was shown that elevated POBF were present in the eye affect by branch RVO when compared to the other eye in the patient and the eyes of the control group. Accordingly, by monitoring and tracking the patient's POBF using the disclosed non-invasive eye measurement technique, RVO can be potentially diagnosed.

Another diagnostic application of the disclosed systems and method is for determining the effectiveness of anti-VEGF therapy. During the progression of multiple ocular diseases, the vascular architecture is altered due to rapid and unorganized neovascularization. This uncontrolled growth of new blood vessels damages the neurons in the retina leading to blindness. Therapy for these sets of conditions is achieved through laser photocoagulation therapy or anti-vascular endothelial growth factor (antiVEGF) injections. Fundamentally, it can be reasoned that reduction in the overall ocular vascular volume results in increased vascular resistance. As such, the overall ocular blood flow is expected to decrease in response to an effective therapy.

As previously discussed, DR is an ocular condition in diabetic people that affects the ocular vasculature. Late stages of DR are characterized by rapid neovascularization that detaches the retinal layer resulting in blindness. One of the treatment options available is laser photocoagulation therapy that aims to block the growth of these vessels. Studies have shown that effective laser photocoagulation therapy can decrease the POBF in patients with proliferative DR. Accordingly, by monitoring and tracking the patient's ocular blood flow using the disclosed non-invasive eye measurement technique, the effectiveness of therapies such as antiVEGF and laser photocoagulation therapy can be monitored.

Another diagnostic application of the disclosed systems and method is for diagnosing/detecting early onset of carotid artery stenosis (CAS). It is known that cardiovascular pressure waveforms can provide information regarding the entire system from the point of measurement till the source of the wave. Eyes are supplied blood by the carotid arteries respective to their side of the body. The carotid arteries detach and separate from the arch of the aorta and as such there is just a small section of overlap between the left and right carotid artery. Given the substantial symmetry of the carotid structure, in a healthy individual the amount of blood supplied by each carotid artery is equivalent. Under the circumstance that an asymmetry develops in one of the arteries, a noticeable pulse waveform difference will become present over time between the two eyes.

CAS is caused by the deposition of plaque over time in the carotid artery resulting in reduced blood flow to the brain and eyes. Typically, this condition is asymmetric and occurs only in one of the two carotid arteries. The biggest complication with this disease is the symptom free progression until a short episode of blood flow interruption occurs, known as transient ischemic stroke. In some embodiments, ocular radial pulsations in both eyes can be compared over multiple measurements to highlight critical differences in the pulse amplitude, which can be an indicator for CAS. Accordingly, by monitoring and tracking the patient's ocular radial pulsations in both eyes using the disclosed non-invasive eye measurement technique using the disclosed non-invasive eye measurement technique, early detection of CAS can be accomplished.

Another diagnostic application of the disclosed systems and method is for measuring and monitoring 3D motion features of the eye to diagnose eye diseases such as keratoconos and staphyloma. The propagation of pressure waves is a phenomenon observed throughout the entire cardiovascular system. Pressure waves are generated from the heart and propagate at a speed that is determined by the fluid's density and confining material's structural properties. In cardiology, it has been well recognized that measuring the pulse wave velocity (PWV) is an indication of cardiovascular rigidity. As the eye is connected to the cardiovascular system and undergoes pulsations during each heartbeat, it can be expected that pressure wave also propagate at the ocular level. These pressure wave propagations are reflective of the fluctuating intraocular pressure with the incoming pulsatile from each cardiac cycle. The speed of wave propagation will be dependent on the material properties of the sclera. In some embodiments, the disclosed systems and methods use the body generated impulses to observe waves on the scleral surface in order to measure the material properties of the sclera.

Alternatively, scleral material properties can also be measured through external generation of waves on the surface of the eye. Waves can be generated by using a vibrating probe on the eyelid section overlaying the sclera. Contacting the eye on a skin covered section allows to perform the entire procedure painlessly. In some embodiments, non-invasive surface curvature measurements can be combined with wave data obtained from a vibrating probe to measure the scleral elasticity.

When a disturbance propagates through an elastic medium, the disturbance can be represented by the passage of three waves. First, a longitudinal or pressure wave, which oscillates in the direction of motion. Second, a transverse or shear wave, which oscillates perpendicular to the direction of motion, but parallel to the surface. Third, a surface or Rayleigh wave, which oscillates perpendicular to the direction of motion and the surface. These three waves all travel at different speeds, and their respective waves speeds are a function of the material properties like Young's modulus, Poisson's ratio, and density. Because the disclosed systems and methods can measure the surface motion in 3D, all three wave motions can be determined from at least the stereo model of the eye, which is generated using a plurality of images. Accordingly, the relationship between the wave speeds can be used to determine the material properties that the disturbance passed through. In other words, by measuring the 3D motion of features on the surface of the eye at sufficient spatial and temporal resolution, the material properties of the eye can be inferred. These properties can be used to diagnose conditions involving changes in the strength of the eye such as keratoconos and staphyloma or to calibrate eye pressure measurements for the individual patients' eyes.

Another diagnostic application of the disclosed systems and method is for detecting heart related side effects. Ocular radial pulsations have been shown to be directly correlated to the heart's pumping activity as the eye pulsates in sync with the heartbeat rhythm. A healthy heart functions with a constant pumping rhythm such that enough nutrients are supplied to the body for correct functionality. Abnormal heart rhythms such as a heart beating too quickly, too slowly or with irregular intervals are reflected in ocular radial pulsations. Thus, in some embodiments, several consecutive ocular radial pulsations can be measured and analyzed for various cardiovascular conditions such as, but not limited to, tachycardia, bradycardia, arrhythmias and premature contractions. Additionally, several medications for both ocular and non-ocular medical conditions have shown to have side effects that affect the heart's pumping activity. In these cases, it is important to recognize the symptoms at an early stage and intervene to avoid complications. Accordingly, by monitoring and tracking the patient's ocular radial pulsations using the disclosed non-invasive eye measurement technique, various heart conditions (e.g., tachycardia, bradycardia, and arrhythmias) can be potentially detected.

Another diagnostic application of the disclosed systems and method is for measuring vessel lumen dilation or contraction. For this application, it should be noted that the vasculature throughout the human body actively expands or contracts its lumen in response to different stimuli. Both the inner and outer surface of the eye are covered with vasculature that exhibits this active response behavior. This active modulation of vessel lumen size can be induced by medical conditions or by molecule imbalances in our blood stream. An example of a medical condition that affect vasculature includes diabetic retinopathy. Some examples of blood molecular imbalances can also cause vasodilation including hyperglycemia and excessive alcohol intake. In some embodiments, the disclosed systems and methods are configured to image the sclera to highlight the vascular structure with sub-pixel accuracy while simultaneously resolving the scale. This is not practically possible with conventional invasive measurement systems.

Non-invasive Measurement System

FIG. 1 is a diagrammatic overview of an example embodiment of a system 100 for measuring one or more characteristics of the eye that can be used to diagnosing a potential medical condition in accordance with some embodiments of the present disclosure. System 100 is shown together with a patient 10 and his or her eyes 20. System 100 includes a light source 101 and imaging sub-system 102 that can capture stereographic (e.g., depth) data of a scene. Light source 101 can be integrated on imaging sub-system 102 or it can be a separate component. Light source 101 can emit light with a wavelength having a range between 300 to 1100 nm. In some embodiments, the light has a wavelength of 400 nm.

Imaging sub-system 102 can include one or more cameras that can capture depth information of a scenery. For example, imaging sub-system 102 can also include one or more RGB-D cameras, which are cameras that can capture images with RGB color information and pixel depth information. The one or more cameras can be high-speed cameras capable of capturing images at a high frame rate, which can range from 30 to 1000+ frames per second. Imaging sub-system 102 can also be a light-based projection system such as, but not limited to, LIDAR (light detection and ranging), structured light, and time of flight.

The one or more cameras of imaging sub-system 102 can include two or more cameras in a stereoscopic alignment (as described with respect to FIGS. 2A and 2B), a telecentric camera with a second off-axis camera, a single defocusing camera with two or more apertures, a general-purpose digital camera, and/or may incorporate technology described in any or all of U.S. Pat. Nos. 6,278,847, 7,612,870, 9,530,213, and 6,229,913. These patents describe suitable hardware for three-dimensional (3D) imaging using various techniques. For example, U.S. Pat. Nos. 6,278,847 and 7,612,870 describe defocusing hardware and methods for determining 3D or depth information based on the separation of features imaged through offset apertures. U.S. Pat. Nos. 9,530,213 and 6,229,913 describe different hardware and methods for determining 3D or depth information from the relative blurring of different images having varying degrees of defocus (hereinafter, "blur-based imaging"). These four patents are incorporated by reference herein in their entirety for all purposes. Alternatively, a stereo imaging camera system may be used for 3D determination.

According to another aspect of the embodiments, imaging sub-system 102 can further include off-axis cameras with Scheimpflug angles configured to give aligned focal planes, folded optics for compactness, and/or custom optics to match the eye curvature of the focal plane. In some embodiments, for example, imaging apparatus can comprise an f-theta lens design and/or include high-speed camera sensors. In other embodiments the imaging apparatus uses a telecentric camera as one of the cameras along with a secondary off-axis camera, where the telecentric camera will have minimal scale change.

Imaging sub-system 102 can be communicatively coupled to a computer 112 (e.g., memory and one or more processors) that can include a 3D-reconstruction module (not shown), a data analytic module (not shown), and one or more diagnostic modules (not shown). These modules can be standalone applications/modules. Alternatively, one or more of these modules can be combined to form an integrated module with functions and features of two or more of the above modules. In some embodiments, computer 112 can also be integrated with image sub-system 102.

The 3D-reconstruction module of computer 112 can reconstruct a 2D or 3D model of a portion of the eye (e.g., blood vessels model, sclera model) using features extracted from images captured by imaging sub-system 102. In some embodiments, the 2D model can be a scale adjusted 2D model configured to capture a snapshot of the local area that is adjusted for the relative displacement of the camera and the eye. In this way, vascular dilation can be better measured. The captured images can contain stereo or depth data (e.g., RGB-D) at different locations of the eye and at different times. For 3D-reconstruction, images with varying focuses and blur rates can also be used to construct the 3D model. In some embodiments, the 3D-reconstruction module can create key points or features on images using algorithm such as, but not limited to, SIFT (scale-invariant feature transform) algorithm, SURF (speeded up robust feature) algorithm to identify and characterize various features of the eye such as blood vessel patterns. It should be noted that a 3D model can be reconstructed using other types of 3D data collection method and 3D data such as, but not limited to, 3D information from LIDAR and light-field camera (e.g., Lytro). Further, consecutive or time-lapsed images (e.g., spatially correlated images) can be combined to de-noise and enhance the measurements. The 3D reconstructed model can contain more information than a mesh or texture, including but not limited to 3D models of one or more portions of the eye, a 3D model of two or more blood vessels in an instant of time or over multiple time steps (e.g., short or long duration), or some other representation of the underlying physical data and measurement certainty.

In some embodiments, the data analytic module of computer 112 can determine one or more characteristics of the eye such as, but not limited to, surface curvature, eye radius, and the approximate total eye volume based on at least the RBG-D data of the captured images and/or the stereoscopic reconstructed model. The data analytic module can also use external measurements such as, but not limited to, axial length of the eye, pupillary distance, age, and sex to refine one or more of the eye characteristics. Using images taken in a time series (e.g., multiple time steps), data analytic module can develop a time-based model of any eye characteristic. For example, a multiple time steps of the surface curvature of the eye can be generated to observe changes in the ocular volume. In another example, changes in the eye radius or eye volume can be observed over time using at least images taken at different times.

In some embodiments, data analytic module can track feature points by matching the feature points across different time steps to produce time lapsed observations of the tracked feature points. Additionally, the data analytic module can perform local spectral analysis such as the frequency domain of the distance between two points over multiple measurements (e.g., 2D deformation) to infer one or more local material properties of the eye. The local material properties can be the strength, elasticity, or thickness of the sclera, for example.

In some embodiments, the data analytic module can generate a bulk 3D shape of the eye or a portion of the eye using one or more images from a single time slice. The images can include stereo, defocusing, and/or RGBD data. In this way, the data analytic module can estimate the bulk parameters of the eye such as, but not limited to, the eye's radius, volume, and surface curvature.

In some embodiments, the data analytic module can generate deformations data of one or more portions of the eye. The data analytic module can track points of interest (e.g., blood vessels) in the eye over multiple time slices. This can provide relative deformation information in addition to bulk 3D information. The data analytic module can also measure ocular pulsation by analyzing the variation of blood flow from heartbeat.

In some embodiments, the data analytic module can generate local frequency or rates of change analysis, which analyzes deformations data and over time to determine the local rates of change through spectral analysis and/or by inferring local relative displacements.

In some embodiments, the data analytic module can generate a model of the local vasculature. This is because the 3D (e.g., stereoscopic) reconstructed model allows for accurate scale resolution that is not be possible with a conventional imaging system. In this way, specific vein or capillaries over time and estimate the dilation or contraction can be measured and tracked.

As previously mentioned, computer 112 can include one or more diagnostic modules (not shown), each of which is designed and programmed to utilize one or more eye characteristics measured by the data analytic module to generate various metrics such as, but not limited to, ocular outflow, ocular deformation, pulse waveform, 2D wave propagation, and ocular pulse waveform variation. In some embodiments, ocular outflow can be determined using at least the bulk 3D shape over multiple time steps and/or using deformation data, which estimates the eye volume or change in the eye volume over a heartbeat.

In some embodiments, the diagnostic module can be programmed to generate a pulse waveform using at least the deformation data, which can be the rate of change of displacement of the eye over a time period. The diagnostic module can also be programmed to generate a 2D wave propagation using at least local frequency analysis and/or deformation data. The 2D wave propagation data can be used to infer various properties of the eye such as the elasticity (e.g., resistance to volume changes) of the sclera.

In some embodiments, the diagnostic module can be programmed to generate waveform variation by tracking a waveform over multiple heartbeats. In this embodiment, a heart monitor can be used to detect the heartbeat.

Various functions of system 100 can be implemented on or with a mobile computing device 110 (e.g., a smart phone or a tablet), using an included camera and on-board processing componentry. Alternatively, mobile computing device 110 may be used for imaging and data display alone communicating wirelessly with the local computing device 106 or remote server 108 for additional processing resources. Alternatively, one or more modules (e.g., data analytic module, diagnostic module) of computer 112 can be integrated on mobile device 110.

According to many of the embodiments, the digital image sensor(s) of imaging apparatus 102 are communicatively coupled to computer processing circuitry included in the system. Furthermore, non-transitory memory (variously located) provides storage for software to run the above processes/modules. IOP-related indications, diagnosis alerts, measurements or estimates that are generated from the digital image sensor data may be output to one or more of display 122 of mobile computing device 110, display 112 of local computing device 106, or any other display communicatively coupled with system 100.

According to other embodiments, imaging apparatus can capture one or more 3D images or video of the sclera of a patient's eye (or eyes). Subsequently, a 3D image reconstruction can be performed and distances between selected point pairs having similar elevations can be measured. Subsequently, a point-pair-distance-to-pressure relationship can be determined based on a standard ocular tonometry performed either previous to or during the same session using pressure-modifying eye drops. In a following session, the sclera can then be re-imaged and an image reconstruction can be performed again. From the subsequent images or image reconstruction, a second set of point pair distances can be measured, compared to the first set of point pair distances, and an intraocular pressure measurement can be determined based on the point-pair-distance-to-pressure relationship.

According to still other embodiments, curvature metrics, instead of point pair distances, can be utilized to estimate IOP change. In these embodiments, imaging apparatus can capture one or more 3D images or video of the sclera of the patient's eye. Subsequently, a 3D image reconstruction can be performed. A first set of curvature metrics can then be extracted from either the images or the 3D-reconstruction, and a curvature-pressure relationship can be determined based on a standard ocular tonometry performed either previous to or during the same session. In a following session, the sclera can be re-imaged utilizing the imaging apparatus, and a 3D image reconstruction can be performed again. From the subsequent images or image reconstruction, a second set of curvature metrics can be extracted, compared to the first set of curvature metrics, and, subsequently, an intraocular measurement can be determined based on the curvature-pressure relationship.

In many of the embodiments described herein, the imaging apparatus can comprise two or more cameras in stereoscopic alignment, a telecentric camera including a second off-axis camera, or a defocusing system with two or more apertures. The imaging apparatus can further include various features such as off-axis cameras with Scheimpflug angles, folded optics, extended depth of field diffraction lenses, or custom optics to match the eye curvature of the focal plane or to minimize changes in scale due to camera position. In some embodiments, the light apparatus can also include various light sources such as, e.g., LEDs, a laser, or a filtered broadband light source.

Figure 2B:
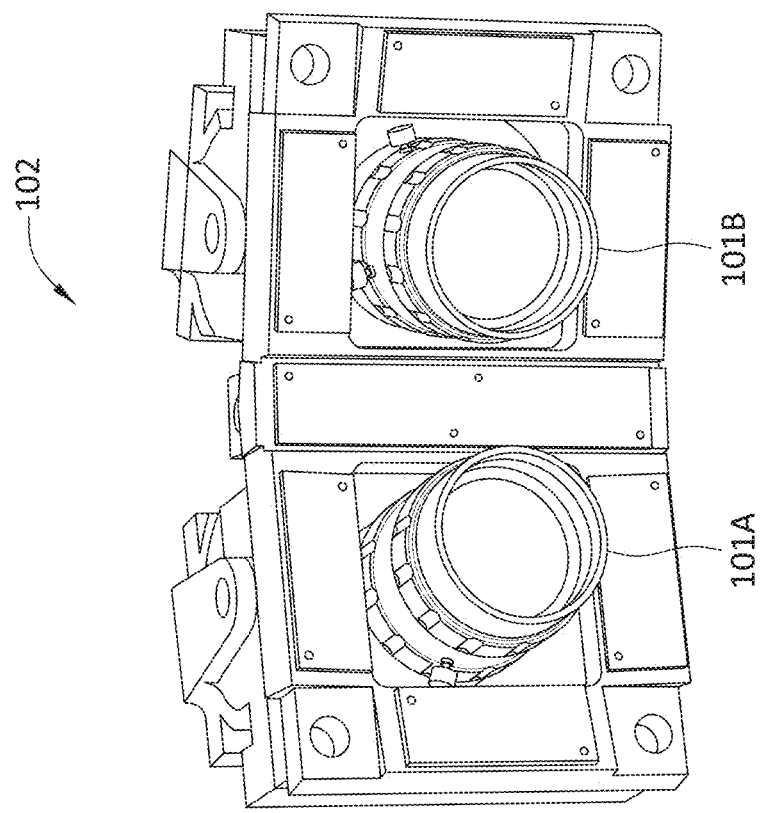
FIGS. 2A and 2B are a photograph and a perspective view, respectively, of an example embodiment of an imaging apparatus for use in a system for measuring ocular properties.
Figure 2A:
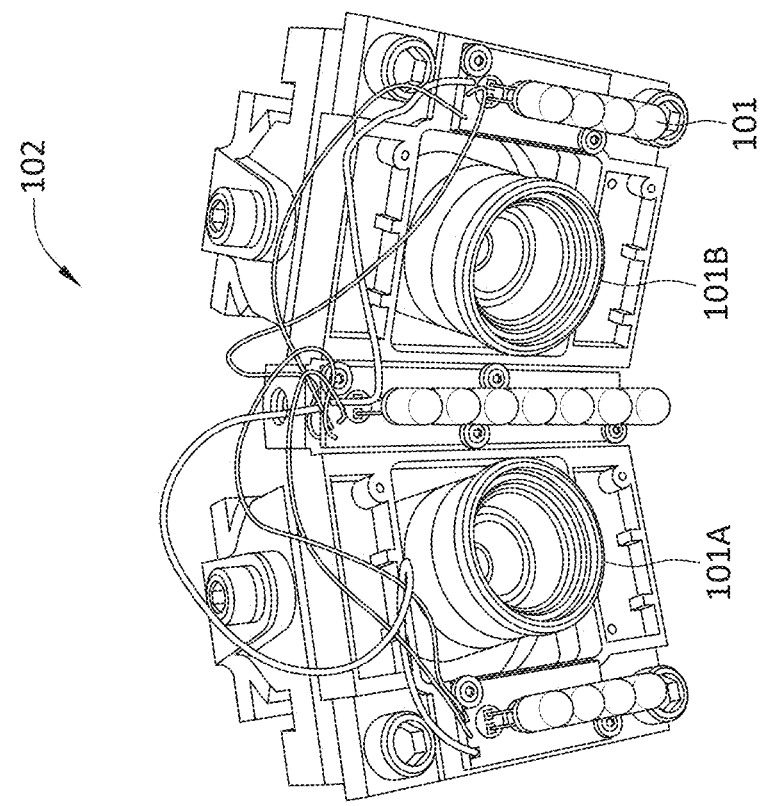

FIGS. 2A and 2B are, respectively, a photograph and a perspective view of one embodiment of imaging apparatus 102 that can be implemented with system 100 for measuring IOP. According to some embodiments, imaging apparatus 102 can include a first camera 101A and a second camera 101B aligned in a stereoscopic configuration. As can be seen in FIG. 2A, imaging apparatus 102 can also include light source 101 configured to illuminate the eye for purposes of digital imaging. Light source 103 can have a wavelength of 300-1100 nm. In some embodiments, light source 103 can have a wavelength ranging from 350 nm to 450 nm to achieve a higher contrast due to the peak absorption of hemoglobin around a wavelength of 400 nm, while avoiding the blue exhaustion band of 450 nm to 480 nm. At 400 nm, the blue light safety hazard coefficient is 10% of the peak at 460 nm, allowing for brighter lights and longer exposures. The contrast afforded at 400 nm allows for imaging finer blood vessels such as those near and around the cornea, which normally would not be visible with a regular imager and illumination. Although FIG. 2A shows an imaging apparatus 102 with light-emitting diodes (LEDs), light source 103 can also include a laser or a filtered broadband light in addition to or instead of the LEDs. In some embodiments, imaging apparatus 102 can also include a light source configured to generate light at near-infrared (IR) wavelengths for imaging the iris. In some embodiments, the light source can have a wavelength ranging from 395-405 nm as certain LEDs are configured to emit light over a certain spectrum width.

Calibration

With respect to IOP, the current gold standard for measuring IOP is the Goldmann Applanation Tonometry (GAT), which uses a small medical probe to contact the cornea with a variable force to create a defined area of applanation. This force is then related to the pressure within the eye through the following equation, $$P = F/A + M - N \quad (1)$$

where P is the pressure inside the eye, F the force applied, A the area of applanation, M the surface tension caused by the tear film, and N is the reaction force of the cornea. For GAT to work, several assumptions regarding the eye's geometrical and viscoelastic properties were made. For example, the scleral rigidity and ocular size are assumed to be constant amongst patients. This was necessary to have a universal relationship for pressure to volume conversions. However, these assumptions proved to be an oversimplification of the complex nature of the ocular system. During aging and onset of ocular diseases, the architecture and material properties of the eye are altered, deviating from the GAT assumptions, which manifested in high interpatient variability and IOP measurement inaccuracy. Corrections factors have been proposed to account for the shortcomings of the GAT system. However, GAT is still inherently inaccurate and is a contact test, which can be very uncomfortable and inefficient. The disclosed systems and methods for measuring IOP uses a calibration approach that addresses all of aforementioned shortcomings of GAT.

To better understand the disclosed calibration method of system 100, an overview of the eye and cardiovascular system is provided. In general, the pulsatile pressure wave generated by the human heart propagates throughout the cardiovascular system. These waves reach the eye through arterial vessels resulting in periodic IOP oscillations. The harmonic component of IOP causes volumetric fluctuations in the human eye. The magnitude of this oscillation depends on the hemodynamic and material properties of the sclera. In general, aging causes important changes in the properties of the sclera which are patient specific. Various parameters including but not limited to sclera thickness, elasticity and mean IOP define the ocular response to fluctuating pressure forces. Following this reasoning, extracting information about material properties from the ocular pulse waveform is an important objective in performing patient specific measurements.

Exploiting the same conceptual idea as in applanation tonometry, the force generated by the incoming pressure wave can be used to obtain patient-specific information and thus measure the intraocular pressure more accurately without the need to contact the surface of the eye. In this respect, the IOP fluctuations can be interpreted as stress variations on the eye. The IOP can be taken as force per unit area exerted on the sclera. Thus, the volumetric expansion of the eye is directly related to force exerted through IOP and the wall's material properties through resistance to deformation. Accordingly, the magnitude of the IOP inside the eye can be calculated by measuring and characterizing the ocular response to an incoming pressure wave.

FIGS. 3A and 3B illustrate examples calibration models 300 and 350, respectively, in accordance with some embodiments of the present disclosure. FIG. 3A illustrates a Kelvin solid model for ocular viscoelastic and flow resistance properties. FIG. 3B illustrates a simplified Kelvin model 350 of model 300 shown in FIG. 3A. Given the viscoelastic properties of the sclera, model 300 includes springs and dashpots to mimic the ocular response to an incoming pressure wave. Model 300 is a mathematical model developed to analyze the behavior of the sclera under stress. Although model 300 can be used to collect multiple measurements at a single time point, a single value measurement can be performed. To this end, model 300 assumes IOP is the only force inducing stress on the sclera. In this representation, the spring (S1) and dashpot (D1) are placed in parallel to mimic the material viscoelastic properties, and the spring (S2) represents the flow resistance. While model 300 characterizes the overall stress-strain response of the eye, further simplification can help derive a more practical pressure-strain relationship. For this calibration, the strain response of the eye to the incoming pressure wave is characterized. To achieve this objective, a further simplified model 350 is developed, which also mimics the viscoelastic strain response of the sclera. Both models rely on the eye having an elastic and linear response to physiological stresses, and not undergoing deformation during hysteresis. Similar assumptions are already used in the clinic for applanation tonometry.

The governing equation for model 350 presented relates pressure to strain in the following relationship, $$p(t) = D\varepsilon(t) + E\frac{d\varepsilon(t)}{dt} \qquad (2)$$

Where p is the IOP, $\varepsilon$ is the strain, D is the elasticity constant and E is the retardation time constant.

Figure 4A:
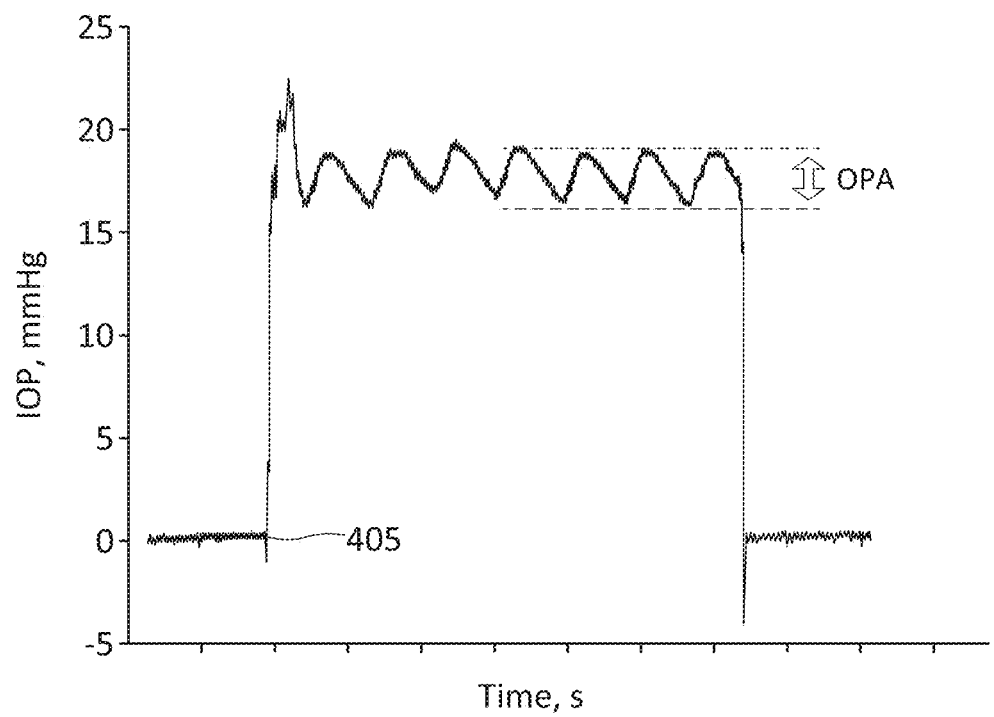
FIGS. 4A and 4B illustrate ocular pulse diagrams in accordance with example embodiments of the present disclosure.
Figure 4B:
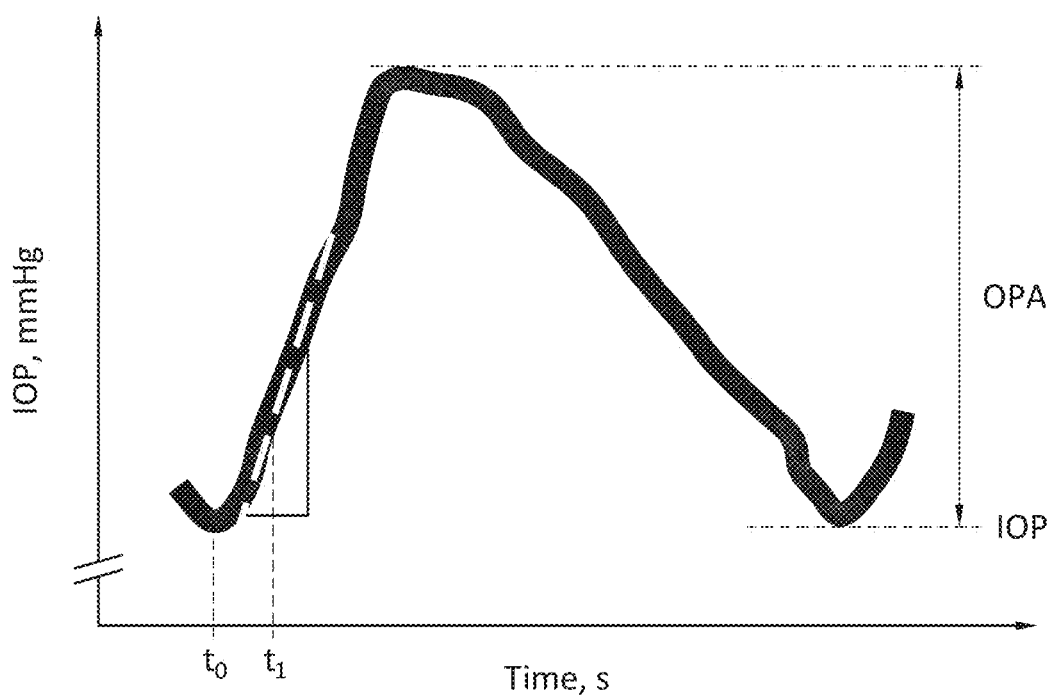

To mathematically analyze a single IOP fluctuation, a reference frame for the system is necessary where time zero will be set at the instance in which the sclera begins a positive volumetric expansion (see to in FIG. 4B). Model 350 includes two parameters that characterize the viscoelastic response of the sclera to the pressure wave. These are the maximum strain change and the delay of maximum strain change from time zero. The maximum strain change will be an indicative measure of the sclera's stiffness. The delay of maximum strain change from time zero is an approximate measure of the retardation time. An example of how to extract these parameters from the ocular pulse wave has been shown below (see FIG. 4B). The pulse waveform can be measured using the method described in U.S. Publication No. 2017/0209046, which is incorporated herein in its entirety. The described method allows multiple strain measurements to be measured from a single timepoint.

With the patient specific ocular parameters obtained from the pulse waveform, the mathematical model can be used to relate the strain to pressure. The retardation time will be a function of the difference between ti and to (see FIG. 4B). In some embodiments, ti is the moment of maximum slope. The elastic modulus will be a function of the maximum strain change and the retardation time. The parameters obtained from the ocular pulse wave will require adjustment with patient data to be implemented in the proposed model to calculate IOP. Model 350 can be used to infer patient specific parameters that can be used to calculate the IOP magnitude. More complex model can be also developed to use pulsatile IOP for the same purpose. This patient specific IOP fluctuations can also be used for diagnostic purposes not limited to glaucoma.

For IOP applications, system 100 can be calibrated using deformation data to fit a displacement model. For heart data calibration such as systolic/diastolic, relative pressure changes due to systolic/diastolic changes from heart beats can be measured as systolic/diastolic changes can causes variations in IOP. This would allow a single point calibration.

For pulse waveform calibration, the estimated radius of curvature of the eye along with the rate of outflow can be used for calibration. This allows a single point measurement to infer the Young's modulus of the eye. For example, the Young's modulus can be calculated by measuring local changes such as wave propagation through the eye using images captured at a high frame rate.

To calibrate system 100 for measuring material properties, local wave propagations and bulk parameters such as radius of curvature, blood pressure, and axial curvature can be used to estimate a calibrated model without a reference calibration.

Example Embodiments of Methods for Measuring Intraocular Pressure

Figure 5:
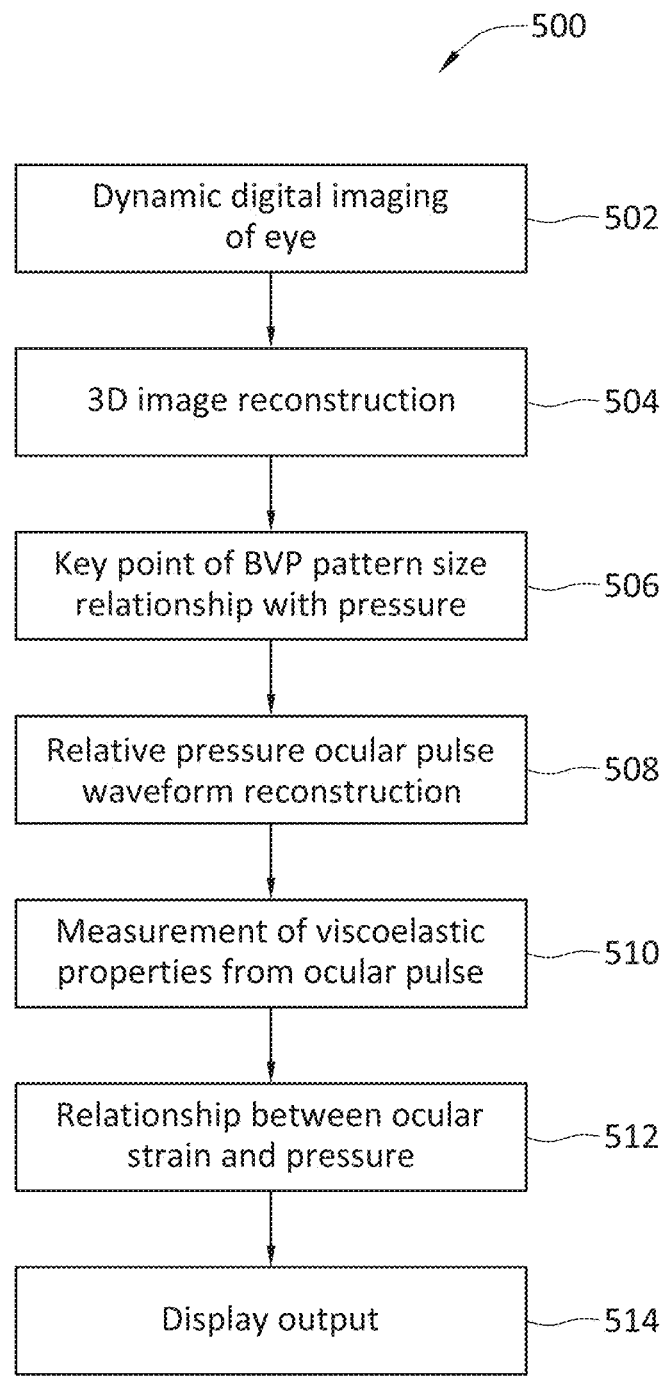
FIG. 5 illustrates a process for ocular measurements in accordance with example embodiments of the present disclosure.

FIG. 5 illustrates a process 500 for calculating IOP of a patient in accordance with some embodiments of the present disclosure. Process 500 starts at 502 where a dynamic digital image of the eye is obtained using an imaging system such as system 100. Here, a plurality of images of the eye can be taken of the eye to be used for stereoscopic 3D-reconstruction at 504.

At 506, keypoint and/or pattern recognition of the blood vessels pattern (BVP) is performed using features recognition and matching algorithm such as SIFT or SURF. At 508, ocular pressure pulse waveform is reconstructed by measuring and tracking one or more BVPs (see FIG. 4A). At 510, the viscoelastic properties (e.g., elastic modulus, retardation time) are measured from the ocular pulse (see FIG. 4B). At 512, the IOP pressure can be derived using the ocular strain and pressure relationship described by equation (2).

FIGS. 6A to 6D are flow diagrams depicting example embodiments of methods for measuring IOP, any of which can be implemented using the systems and apparatuses described with respect to FIGS. 1, 2A, 2B, 3, 4, 5, and elsewhere throughout the present disclosure. As an initial matter, those of skill in the art will understand that the method steps disclosed herein can comprise instructions stored in non-transitory memory of a local computing device, mobile computing device, and/or remote server, and that the instructions, when executed by one or more processors of the local computing device, mobile computing device, or remote server, can cause the one or more processors to perform any or all of the method steps disclosed herein. Furthermore, those of skill in the art will appreciate that any or all of the method steps disclosed herein can be performed by a single device (e.g., local computing device) or, in the alternative, can be performed across various devices in geographically dispersed locations.

Figure 6A:
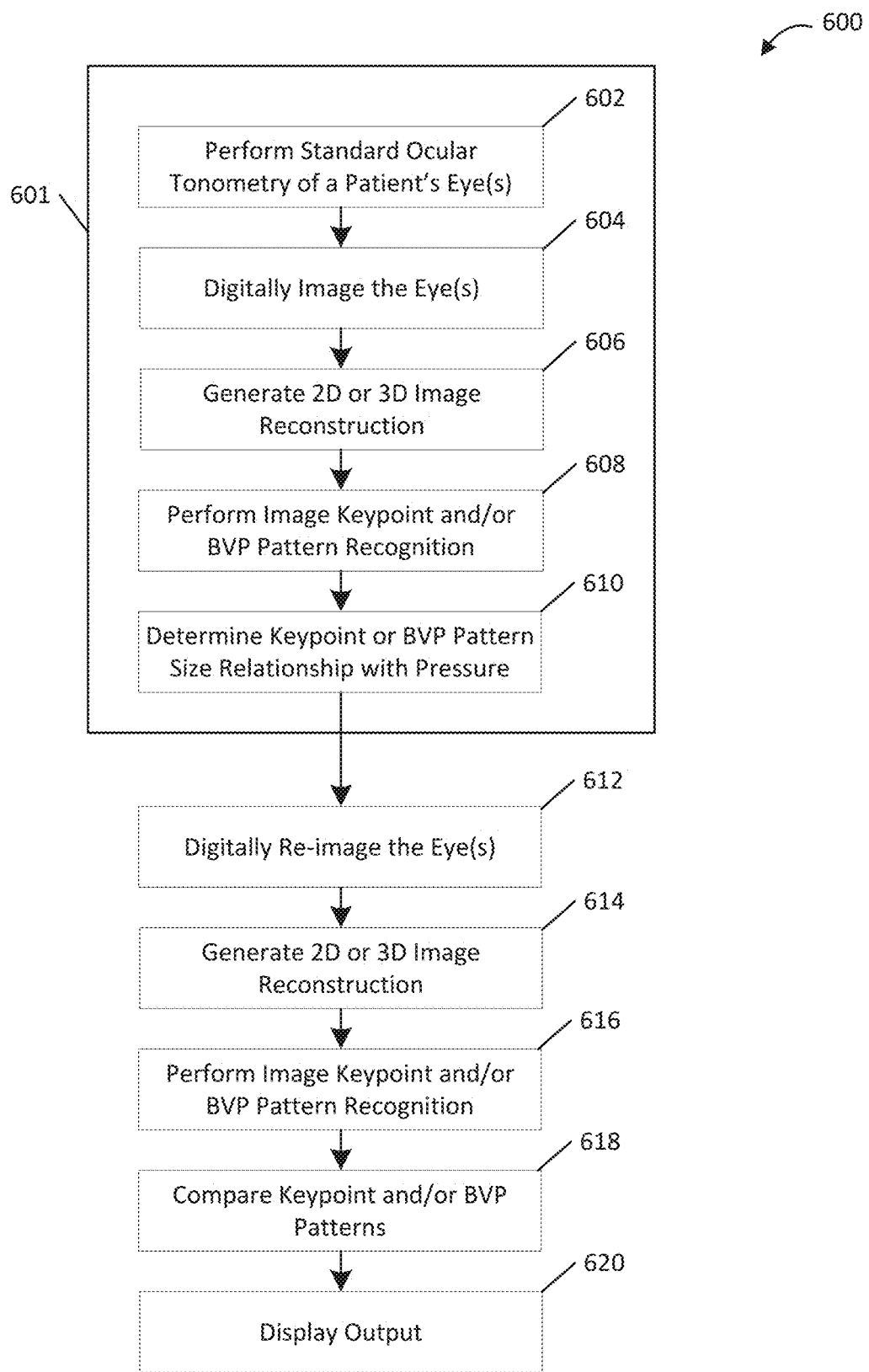
FIG. 6A to 6C are flow chart diagrams depicting example embodiments of methods for ocular measurements.

Turning to FIG. 6A, a flow diagram depicts an example embodiment of a method 600 for measuring IOP. In the same seating or setting as the remaining method steps, or in a prior appointment with an ophthalmologist, as indicated by box 601, a set of calibration data (e.g., typically a minimum of two points for each eye of a given patient) is obtained at Steps 602, 604, 606, 608, and 610.

More specifically, at Step 602, standard ocular tonometry of a patient's eye (or eyes) can be performed using pressure modifying eye-drops. Subsequently, at Step 604, the sclera of the eyes can be digitally imaged (e.g., by digital photography or videography) using any of the imaging apparatuses described with respect to FIGS. 2A, 2B, 5, and elsewhere throughout the present disclosure. In some embodiments, each eye may be imaged in one scene or frame. In other embodiments, multiple scenes or frames may be captured to allow an imaging apparatus with a smaller field of view to interrogate the entire eye. According to one aspect of these embodiments, the imaging apparatus can be configured to capture an image of a blood vessel pattern (BVP) against the contrast of the white sclera.

Subsequently, at Step 606, a two-dimensional (2D) or three-dimensional (3D) image reconstruction can then be generated based on the captured images. In some embodiments, if multiple time points or frames of the eye are captured, a 2D or 3D "reconstruction" can be produced by "stitching" together the images. For 3D-reconstruction, image processing using defocusing, blur-based imaging or stereo imaging can be employed to form a 3D model. In 2D or 3D, the 3D-reconstruction process may also or alternatively involve creating identifiable keypoints (such as ORB, SIFT, SURF, or neural network-derived features) involving or characterizing the included blood vessel patterns contrasted by or against the sclera. When capturing subsequent images by each camera, information of spatially correlated image patches can be combined to de-noise and enhance the measurements. This method can also be used to create higher resolution models of those patches for more accurate IOP determination.

At Step 608, keypoint and/or pattern recognition of the BVP (e.g., by using SIFT software or other feature matching and stitching algorithms) may be performed. Together, at Step 610, these data are variously analyzed (i.e., all such data may be used or only a subset thereof used) to establish a pressure-BVP-size relationship. These steps (optionally taken together and performed in a separate procedure, as indicated by the box indicating Step 601) produce a calibration data set relating eye pressure to the BVP across the sclera of at least one human eye.

After producing the calibration data set, one or both eyes are digitally re-imaged or imaged for pressure measurement at Step 612 (through the same or similar methods described with respect to Step 604). This step may be performed in the same setting or session (e.g., once a patient's ocular pressure is no longer influenced by the use of drops, or otherwise). Alternatively, it may occur at a later date in one or more follow-up visits to a clinic or other outpatient setting. Generally, such visits will be separated in time on the order of several months. In the case of monitoring for IOP, yearly changes associated with volume and/or BVP scale change (in which no calibration data is produced per Step 610), or in the full method in which calibration data is employed may be observed over a patient's lifetime.

At Step 614, a 2D or 3D image reconstruction is again performed based on the image(s) captured at Step 612. Then, at Step 616, pattern recognition techniques can again be applied to the 2D or 3D-econstruction characterizing the BVPs. At Step 618, keypoints and/or pattern matching can be performed and compared to that produced or available from the calibration data set produced through the steps shown in box 601. According to one aspect of the embodiments, the comparison (or comparisons, if additional scans are made of the eye after initial calibration data scanning) yields an estimation of scale change.

Together with the pressure-based calibration data, an estimated measurement of IOP can be produced as an output at Step 620. Alternatively, in some embodiments, a comparison of overall volume change (eliminating the need for various keypoints or pattern recognition) and/or scale change BVP features can be made without using calibration data. In some embodiments, for example, the comparison at 618 can be between an earlier image data set and a current or later image data set, and the output at 620 may be a relative indication of change in IOP (e.g., as an alert regarding climbing or escalating IOP). Any such, output may be visually displayed on a monitor of such hardware as referenced earlier, stored in a patient file or database, or otherwise handled.

Figure 6B:
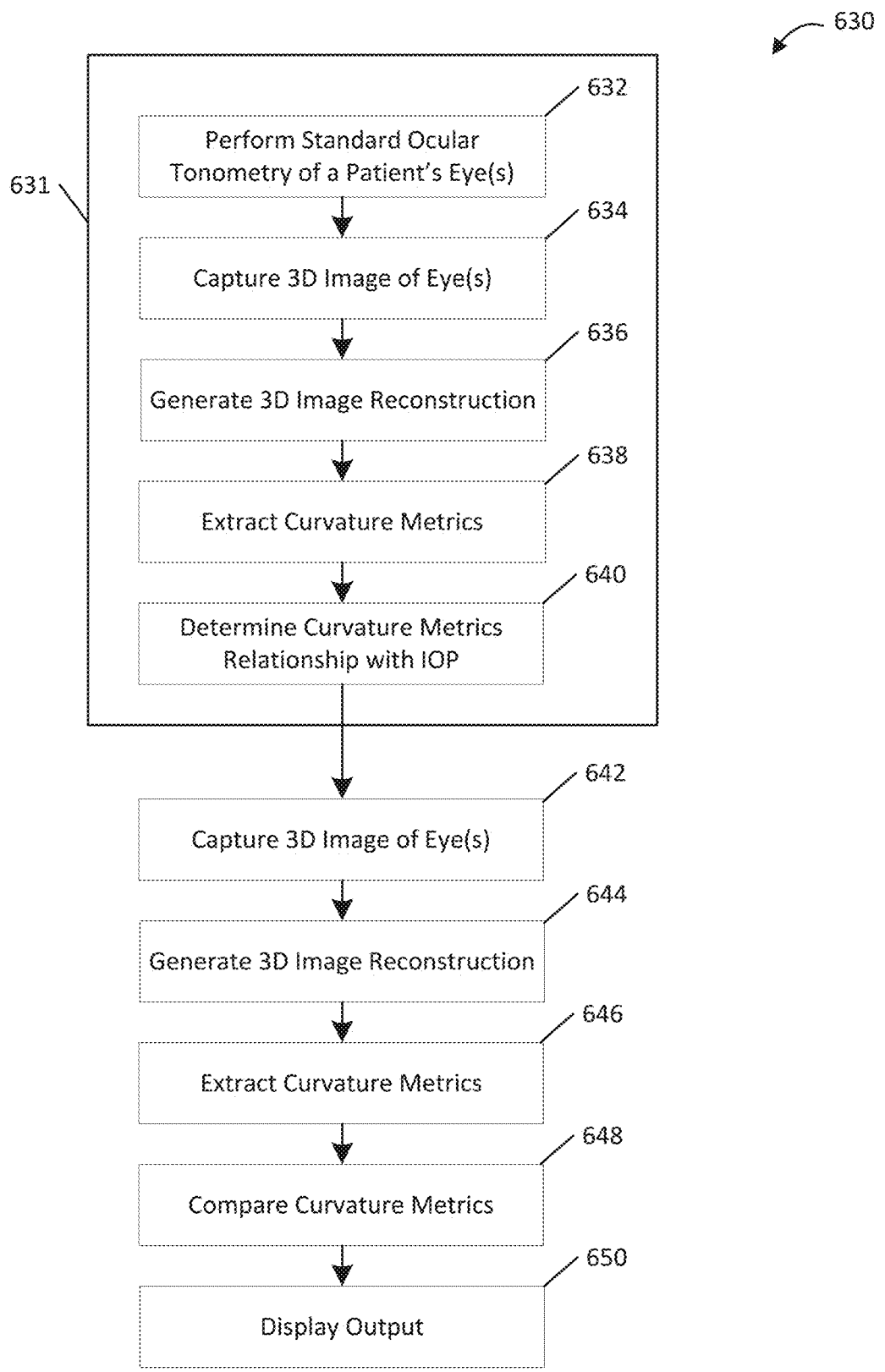

Turning to FIG. 6B, a flow diagram depicts another example embodiment of a process 630 for measuring IOP. Similar to method 600, as indicated by box 631, a set of calibration data is obtained at Steps 632, 634, 636, 638, and 640. More specifically, at Step 632, standard ocular tonometry of a patient's eye (or eyes) can be performed using pressure modifying eye-drops. Subsequently, at Step 634, a 3D image of the eye (or eyes) is captured using an imaging apparatus. According to some embodiments, the imaging apparatus can be configured to utilize stereoscopic and/or defocusing techniques to capture a 3D image of the surface of the sclera of each eye.

Subsequently, at Step 636, a 3D image 3D-reconstruction can then be generated based on the captured image. According to some embodiments, image processing using defocusing, blur-based imaging, and/or stereo imaging can be employed to form a 3D model. At Step 638, a first set of curvature metrics can be extracted from the generated 3D image. In some embodiments, the curvature metrics can include, for example, a mean radius of the sclera. In other embodiments, curvature metrics can also include the local surface curvatures at every point of the 3D image, such as the standard principal curvatures that can be computed from a 3D mesh. Then, at Step 640, these data are variously analyzed to establish a relationship between the curvature metrics and IOP.

After producing the calibration data set, another 3D image of the eye (or eyes) is captured by the imaging apparatus at Step 642. This step may be performed in the same setting or session (e.g., once a patient's ocular pressure is no longer influenced by the use of drops, or otherwise) or, alternatively, at a later date in one or more follow-up visits to a clinic or other outpatient setting. At Step 644, a 3D image reconstruction can then be generated based on the image captured at Step 642, and a second set of curvature metrics can be extracted from the generated 3D image at Step 646.

Subsequently, at Step 648, the second set of curvature metrics can be compared to the first set of curvature metrics to determine an estimation of scale change. Utilizing the IOP-curvature relationship determined at Step 640, an estimated measurement of IOP can be determined and output to a display at Step 650. In some embodiments, the first and second sets of curvature metrics and IOP measurements can also be stored in a patient file or database. Moreover, those of skill in the art will appreciate that Steps 642, 644, 646, 648, and 650 of method 630 can be iteratively repeated, at a later date, to generate additional sets of curvature metrics (to be compared with earlier sets of curvature metrics), in order to track change in a patient's IOP for purposes of diagnosing, monitoring, and treating the progression of an adverse condition such as glaucoma.

Figure 6C:
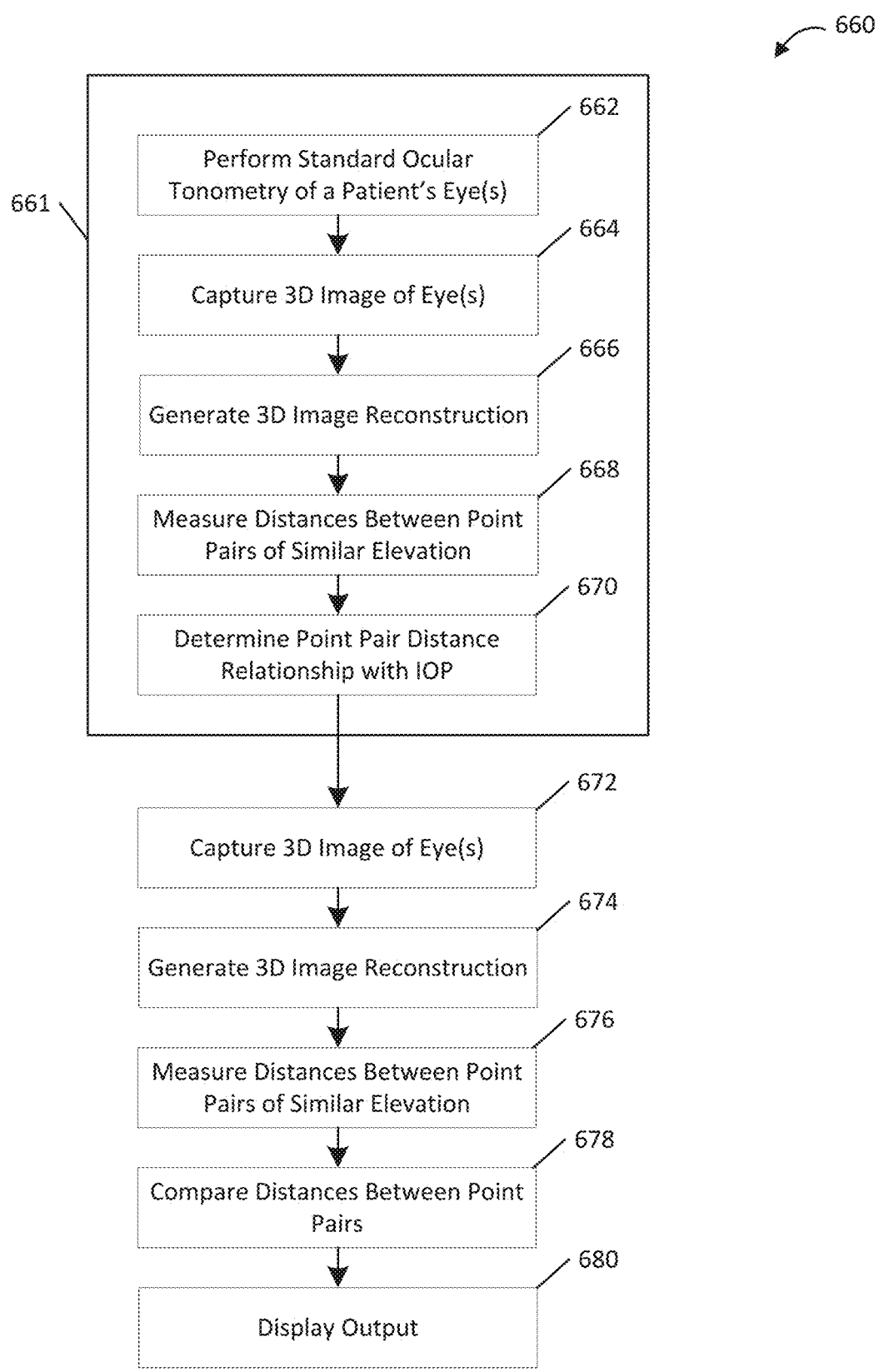

Turning to FIG. 6C, a flow diagram depicts another example embodiment of a process 660 for measuring IOP. Similar to processes 600 and 630, as indicated by box 661, a set of calibration data can first be obtained at Steps 662, 664, 666, 668, and 670. More specifically, at Step 662, standard ocular tonometry of patient's eye (or eyes) can be performed using pressure modifying eye-drops. Subsequently, at Step 664, a 3D image of the eye (or eyes) is captured using an imaging apparatus. In many of the embodiments, the imaging apparatus can comprise at least one telecentric lens. Similarly, the imaging apparatus can be configured to utilize stereoscopic and/or defocusing techniques to capture a 3D image of the surface of the sclera of each eye and/or further configured to capture an image of a blood vessel pattern (BVP) against the contrast of the white sclera. Furthermore, the upper layers of the sclera are attached to muscle and eye movement can cause inaccuracies in the measurements described below. Because the area around the cornea is less affected by muscle strain on the eye, in some embodiments, the imaging apparatus can be positioned and/or configured to image the patient's sclera near or around the cornea.

Subsequently, at Step 666, a 3D image reconstruction can then be generated based on the captured 3D image. According to some embodiments, image processing using defocusing, blur-based imaging, or stereo imaging can be employed to form a 3D model. At Step 668, point pairs of similar elevation are identified in the 3D model and the distances between the points are determined. As described in further detail below, tests show that by using point pairs of similar elevation, distance measurement is more accurate because point x-y localization is generally more accurate than points having different elevations (i.e., along the z-axis). At Step 670, these data are variously analyzed to establish a relationship between the point pair distance and IOP.

After producing the calibration data set, another 3D image of the eye (or eyes) is captured by the imaging apparatus at Step 672. This step may be performed in the same setting or session (e.g., once a patient's ocular pressure is no longer influenced by the use of drops, or otherwise) or, alternatively, at a later date in one or more follow-up visits to a clinic or other outpatient setting. At Step 674, a 3D image reconstruction can then be generated based on the image captured at Step 672, and a second set of measured distances between point pairs of similar elevation can be determined at Step 676.

Subsequently, at Step 678, the second set of measured distances between pair points of similar elevation can be compared to the first set of measured distances to determine a net change of the surface of the sclera. According to some embodiments, this can be determined by utilizing measurement covariance, either through direct calculation or numerical approximation. Utilizing the point-pair-distance-to-IOP relationship determined at Step 670, an estimated measurement of IOP can be determined and output to a display at Step 680. In some embodiments, the first and second sets of measured distances and IOP measurements can also be stored in a patient file or database. Moreover, those of skill in the art will appreciate that Steps 672, 674, 676, 678, and 680 of method 660 can be iteratively repeated, at a later date, to generate additional sets of measured distances between point pairs of similar elevation (to be compared with earlier sets of data), in order to track change in a patient's IOP for purposes of diagnosing, monitoring, and treating the progression of an adverse condition such as glaucoma.

Figure 6D:
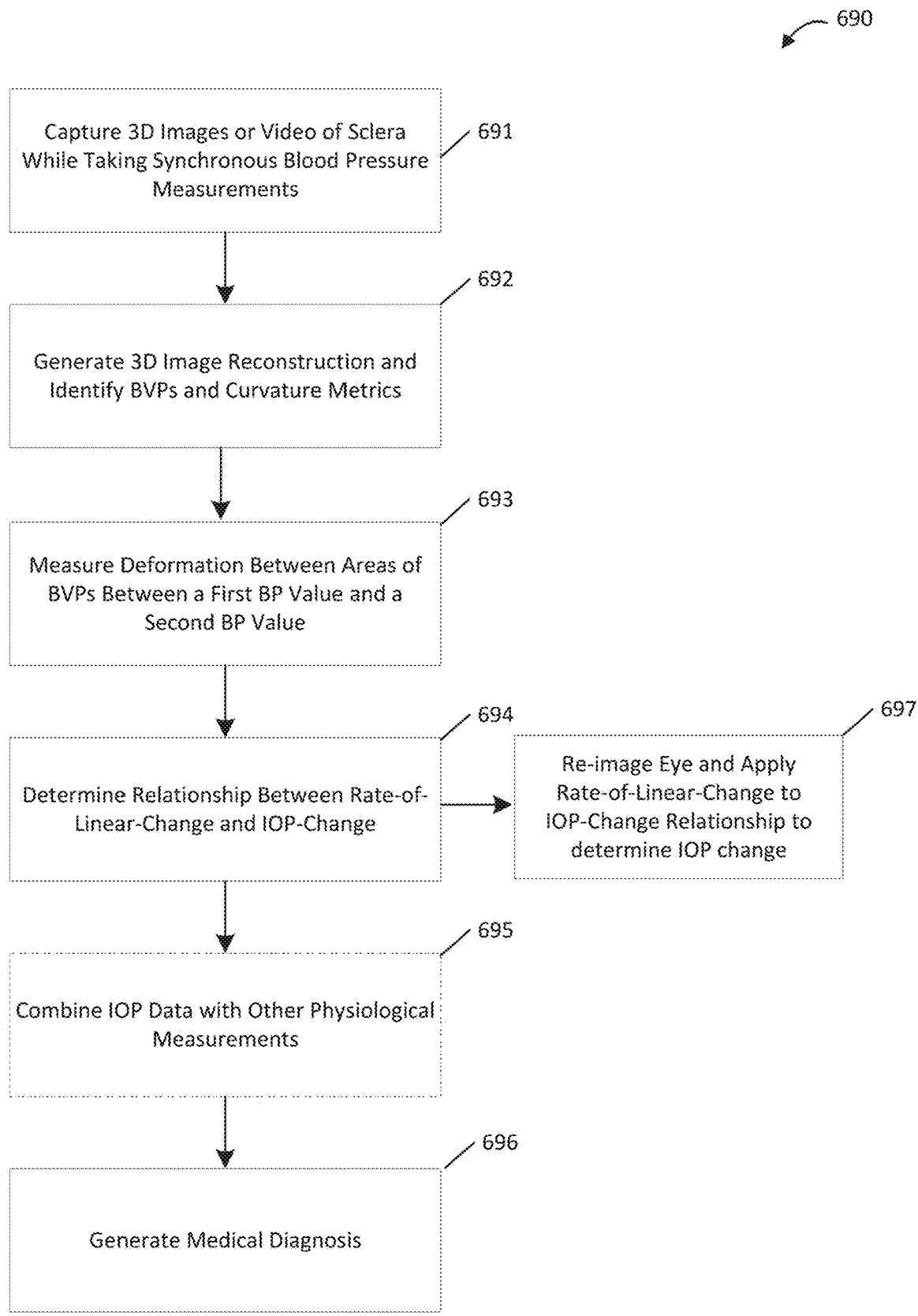
FIG. 6D is a flow chart diagram depicting an example embodiment of a method for medical diagnosis utilizing ocular properties.

Turning to FIG. 6D, a flow diagram depicts an example embodiment of a process 690 for using IOP measurements for aiding in a medical diagnosis. According to one aspect of the embodiments, process 690 operates on the principle that IOP naturally varies with changes in blood pressure caused by the heartbeat. By using captured video image data of the eye as a method for calibrating the relative rate of expansion of the eye relative to IOP, a rate-of-linear-change to IOP-change relationship can be determined and subsequent IOP changes can be measured utilizing the imaging techniques described herein.

Referring still to FIG. 6D, at Step 691, digital images of the sclera are captured using an imaging apparatus comprising one or more high-speed camera sensors. In some embodiments, the imaging apparatus can capture multiple 3D images in rapid succession and/or video of the sclera of the patient's eye (or eyes). In other embodiments, the imaging apparatus can be configured to capture video of the sclera at a rate greater than 30 Hz. Still referring to Step 691, while the 3D images and/or video are being captured, synchronous blood pressure measurements are taken. In addition, a standard tonometry can be performed without the use of pressure-modifying eye drops to obtain a reference IOP measurement. At Step 692, a 3D image 3D-rerconstruction is generated from which blood vessel patterns (BVPs) can be identified and curvature metrics of the sclera can be determined. At Step 693, using the synchronous blood pressure measurements and the 3D image reconstruction, deformation between the areas of BVPs between a first blood pressure value (e.g., a nadir or diastolic blood pressure value) and a second blood pressure value (e.g., a peak or systolic blood pressure value) can be measured. At Step 694, based on the deformation measurement, the reference IOP measurement, and the curvature metrics, a relationship between a rate-of-linear-change relative to IOP-change can then be determined. In subsequent sessions, as shown at Step 697, relative IOP changes in the patient's eye can be determined by re-imaging the sclera and applying the relationship between the rate-of-linear-change to IOP-change. The IOP measurements generated at Step 697 can then be output to a display. Optionally, in some embodiments, at Step 695, the relative IOP changes can be combined with other physiological measurements (e.g., other parts of the body). At Step 696, a medical diagnosis can be generated based on the combination of the IOP measurement(s) and the physiological measurements.

In some embodiments, IOP can be determined by comparing the dilation of blood vessel positions (or other eye features) at different time points. For example, process 690 can construct a 3D model of a portion of the eye and monitor that particular portion at 1 Hz to measure the changes in dilation. Process 690 can also track the variations in dilation as the blood vessels pulsate and measure the average dilation over a certain period of time, which can then be used to measure IOP. Process 690 can also measure IOP based on at least the resistance to pressure by the scleral wall of the eye and outflow resistance of the vasculature.

According to another aspect of the embodiments, encryption can be utilized to secure any of the data acquired or transmitted by any of the systems, devices, and apparatuses described herein, including any of the physiological measurements (including, but not limited to, IOP measurements and blood pressure measurements), medical diagnoses, images captured by the imaging apparatus, image reconstructions, BVP measurements (including but not limited to point pair distances), curvature metrics, deformation values, rate-of-linear-change to IOP-change relationships, and the like. Those of skill in the art will also appreciate that such data can be encrypted in storage or in transit, for example, through the use of public and private keys, or any desired technique or scheme (e.g., key generation algorithms, signing algorithms, and signature verifying algorithms). These and other suitable examples include, but are not limited to, techniques or schemes based on the RSA algorithms (and their variants), El Gamal algorithms (and their variants), Diffie-Hellman algorithms, Digital Signature Algorithm (DSA) and its variants, elliptical curve-based algorithms and its variants, and/or Rabin algorithms and its variants.

Those of skill in the art will also appreciate that any of the method steps described with respect to methods 600, 630, 660, and 690 are freely combinable with any of the other method steps described within the present disclosure to achieve the result of an intraocular pressure measurement. Likewise, FIGS. 6A to 6D illustrate example embodiments of methods for measuring intraocular pressure and are not intended to limit the order in which the steps are performed, as those of skill in the art will appreciate.

Experimental Data

Figure 7A:
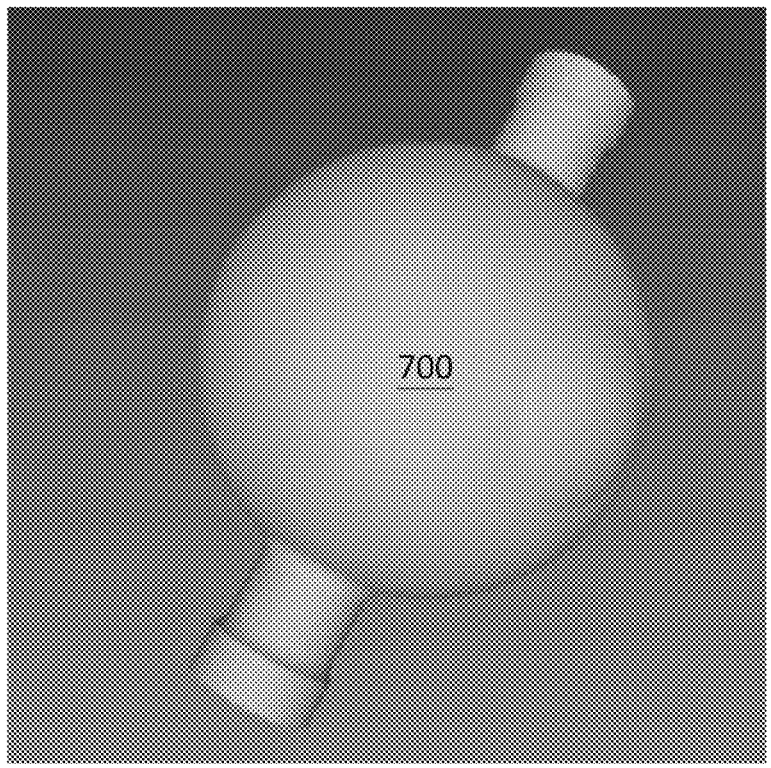
FIGS. 7A and 7B are a perspective view and a photograph, respectively, of a model used for testing an example embodiment of a system for measuring ocular properties.
Figure 7B:
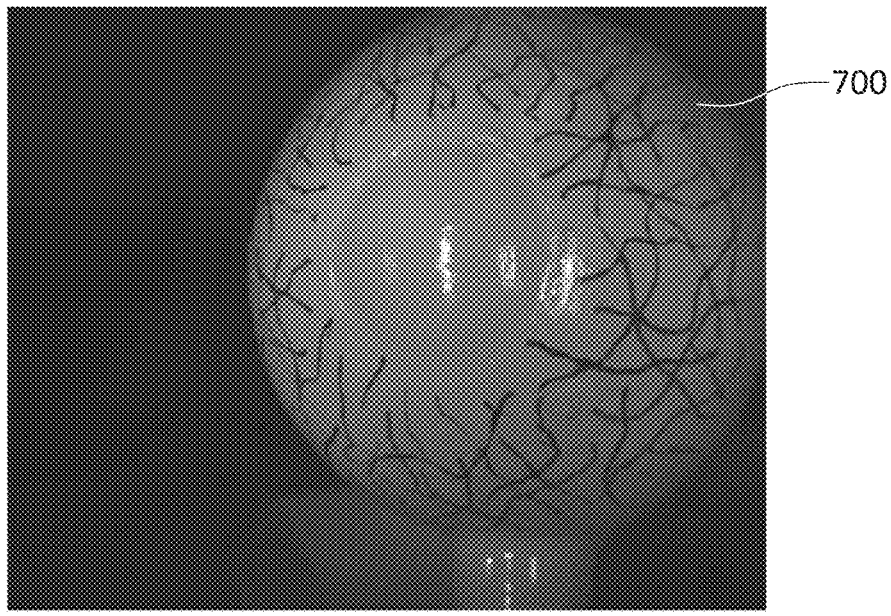
Figure 7C:
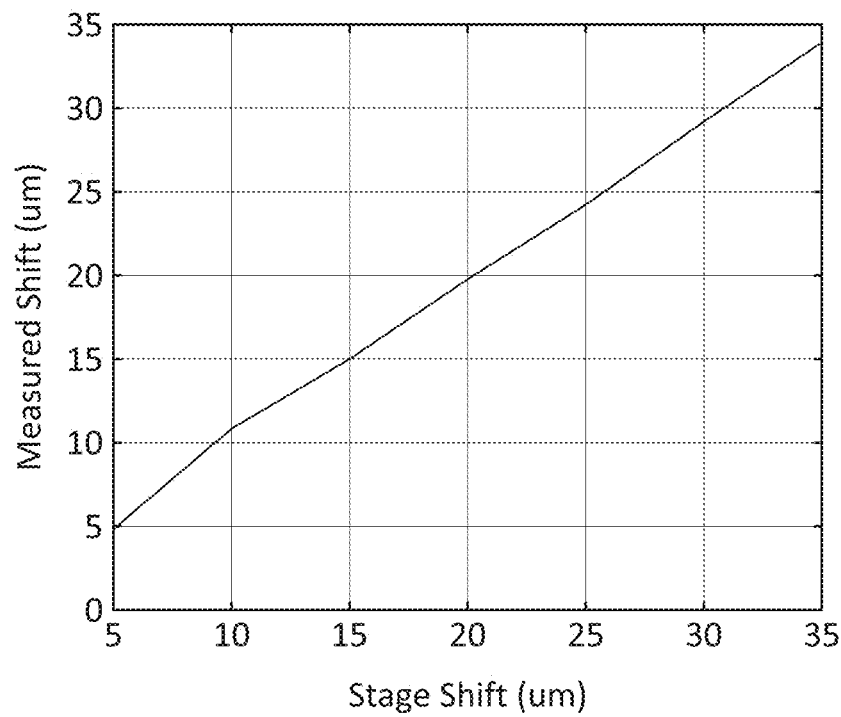
FIGS. 7C to 7E are graphs showing various results from testing of a model by an example embodiment of a system for measuring ocular properties.
Figure 7D:
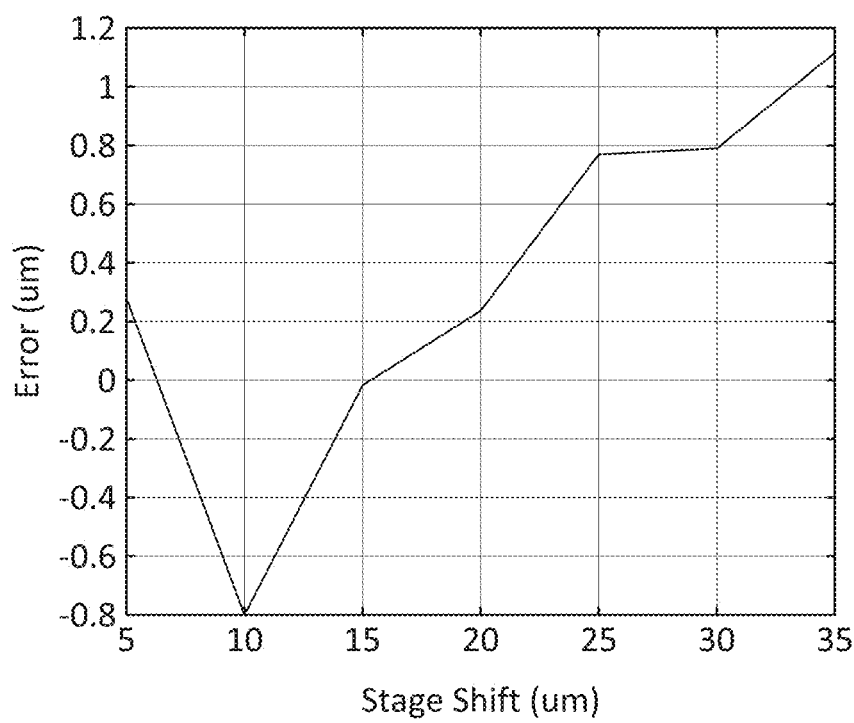
Figure 7E:
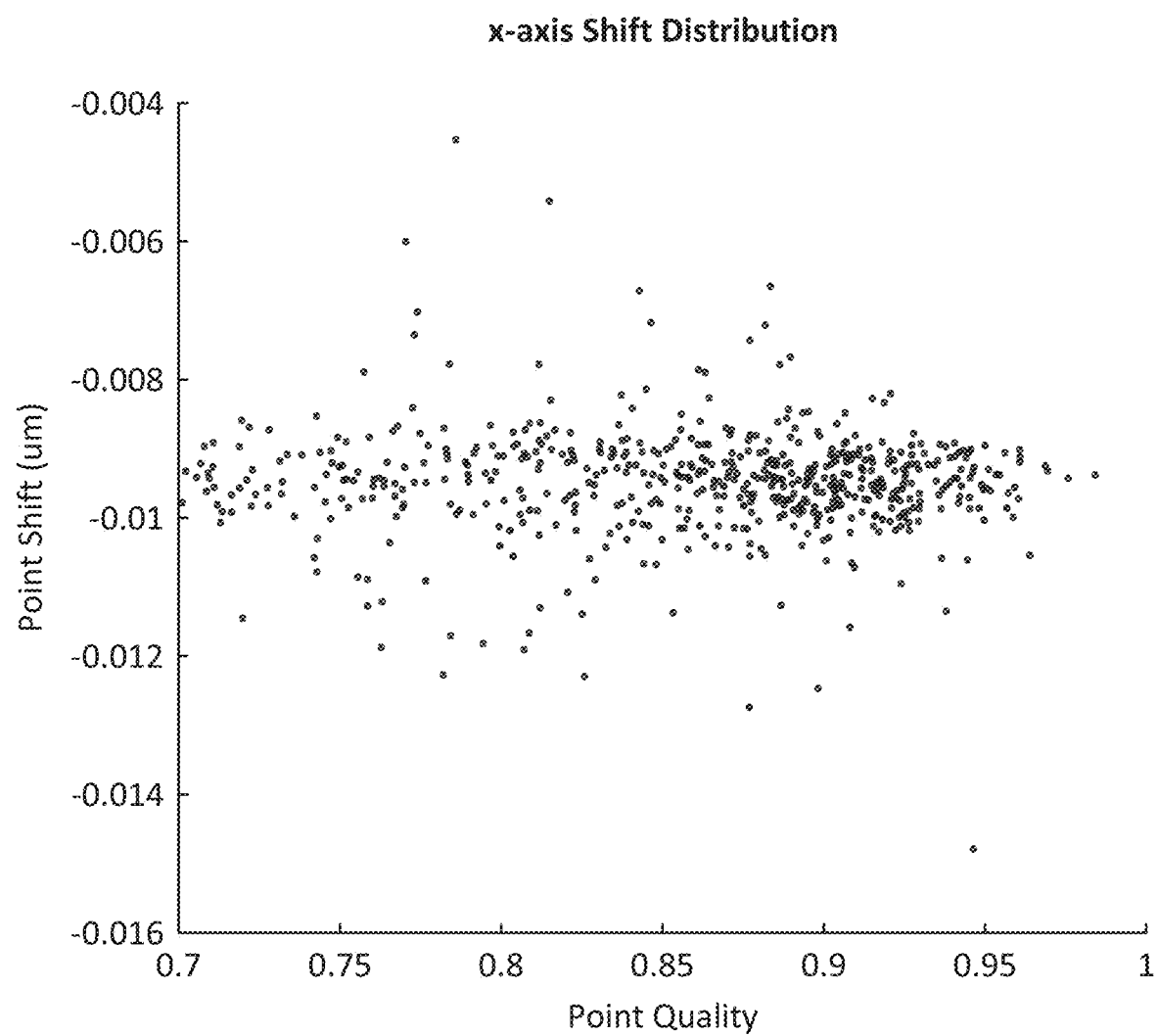

Experiments performed in relation to the embodiments of the present disclosure will now be described. FIGS. 7A and 7B are, respectively, a perspective view and a photograph of an inflatable model 700 of an eye used for testing an example embodiment of a system for measuring IOP. According to one aspect of the testing, a precision stage was utilized, wherein a target was shifted in 5 um increments while being imaged by an imaging apparatus. In this case, the imaging apparatus comprised two cameras in a stereoscopic alignment with multiple LEDs for providing a light source. Subsequently, key points were extracted and filtered by a quality metric obtained from the images. As can be seen in the test results in the graphs depicted in FIGS. 7C and 7D, the mean shift error was less than 1 um. Furthermore, as shown in the graph in FIG. 7E, the typical standard deviation of high-quality individual x,y point shift errors was found to be between 0.5 um and 1.0 um. By contrast, the typical standard deviation of individual point shift errors around the noise along the z-axis was found to be between 1.0 um and 5.0 um. Based on the aforementioned results, it was determined that x,y point localization (i.e., for point pairs having similar elevation) for high-quality points yielded relatively accurate measurements.

Figure 8A:
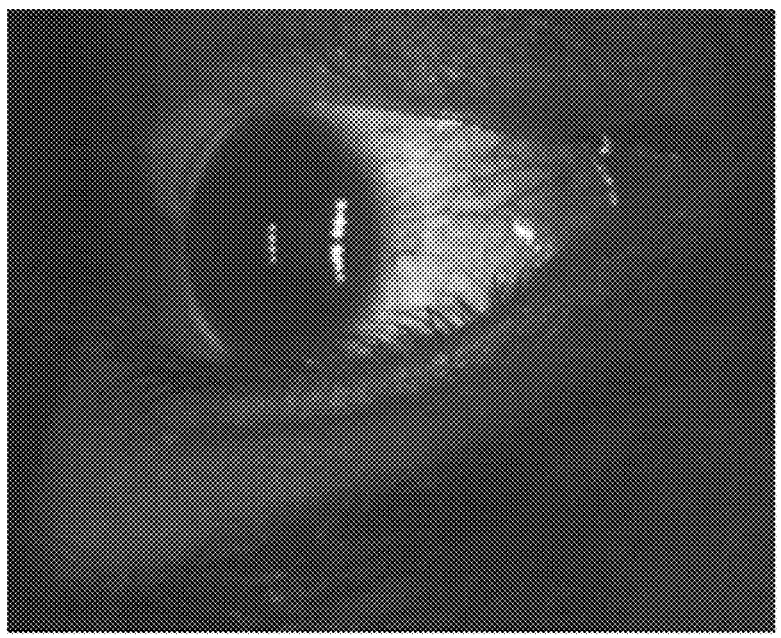
FIG. 8A to 8D are a photographic image and 3D-reconstruction of a subject's eye utilized for testing an example embodiment of a system for measuring ocular properties.
Figure 8B:
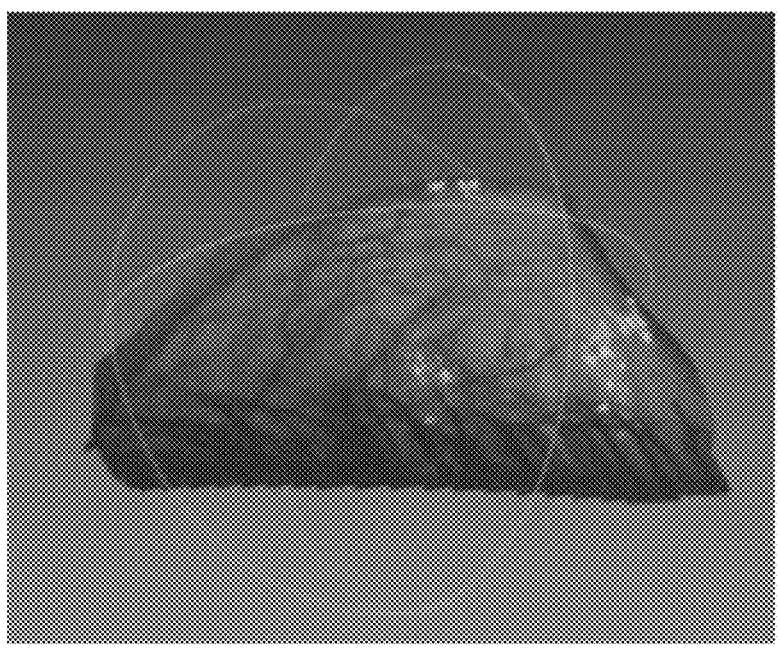
Figure 8C:
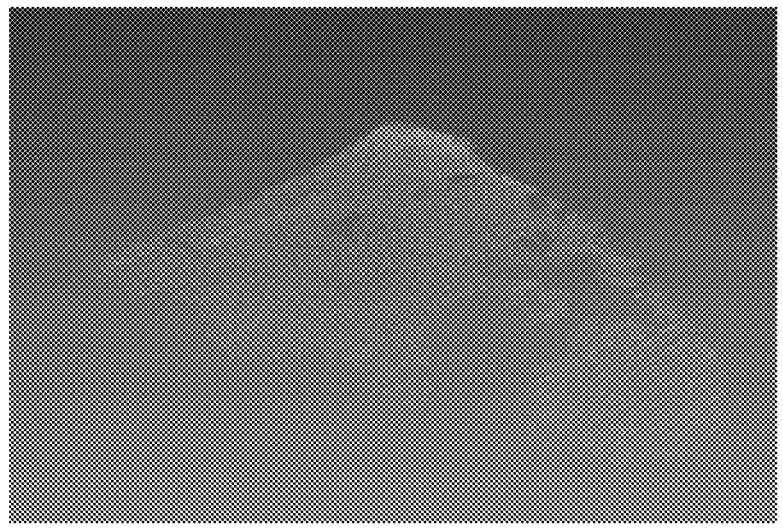
Figure 8D:
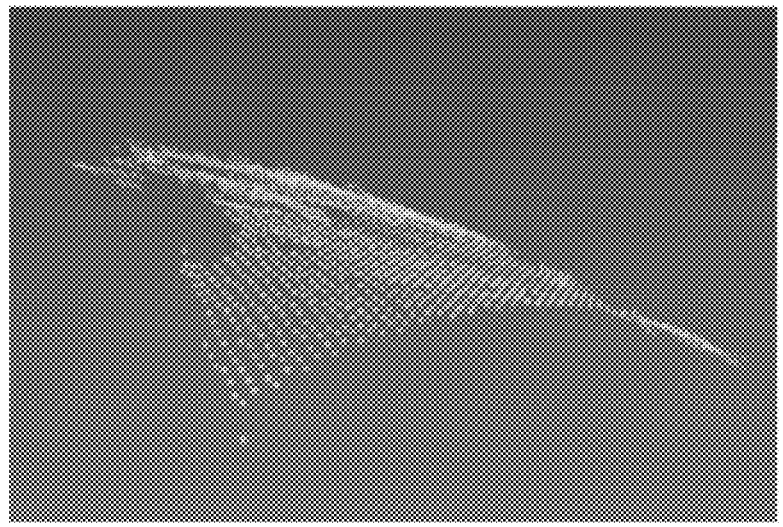
Figure 8E:
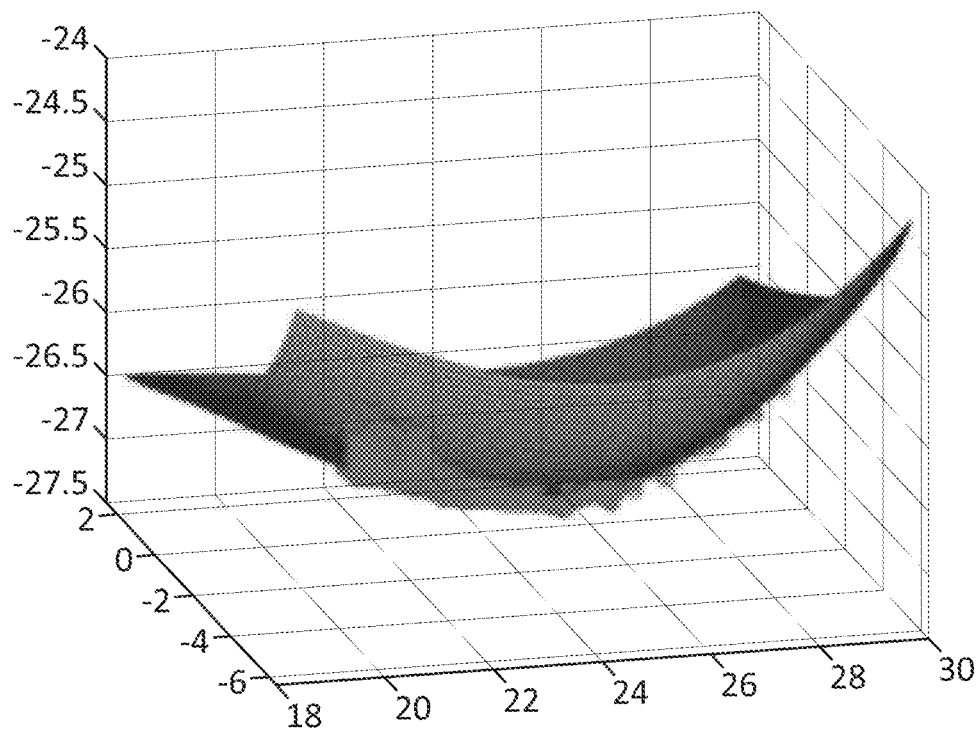
FIGS. 8E and 8F are 3D reconstructed images based on testing of an example embodiment of a system for measuring ocular properties.
Figure 8F:
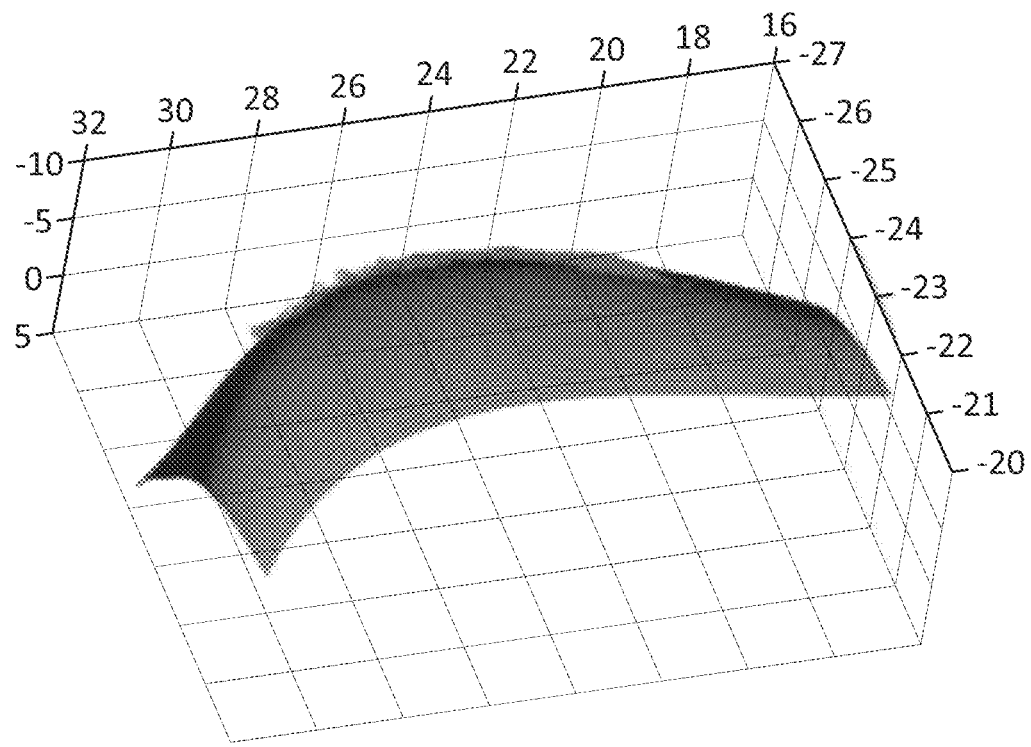
Figure 8G:
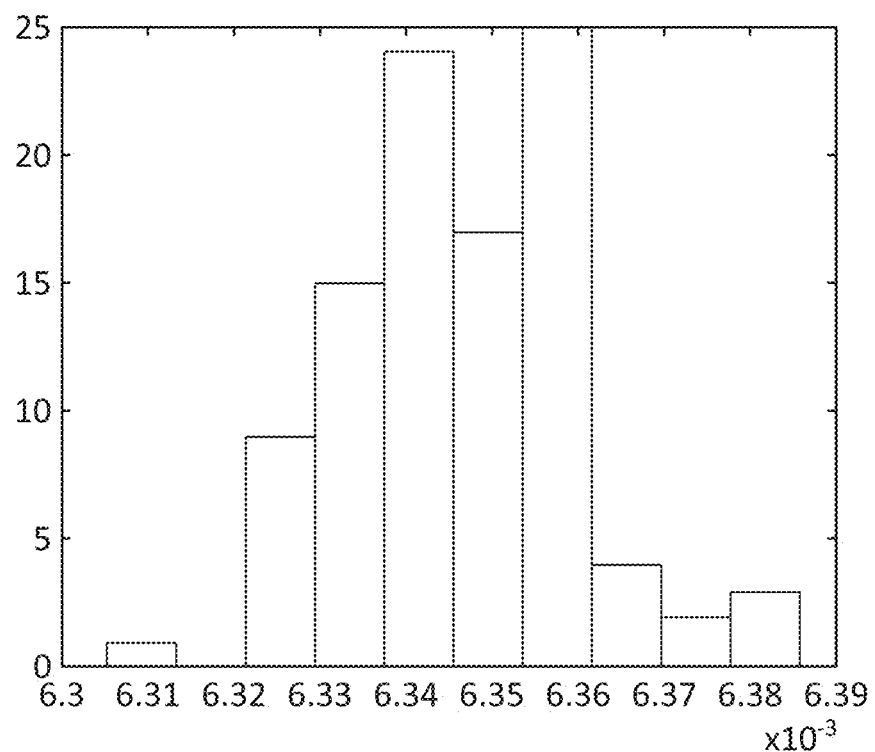
FIGS. 8G and 8H are graphs depicting curvature measurements based on testing of an example embodiment of a system for measuring ocular properties.
Figure 8H:
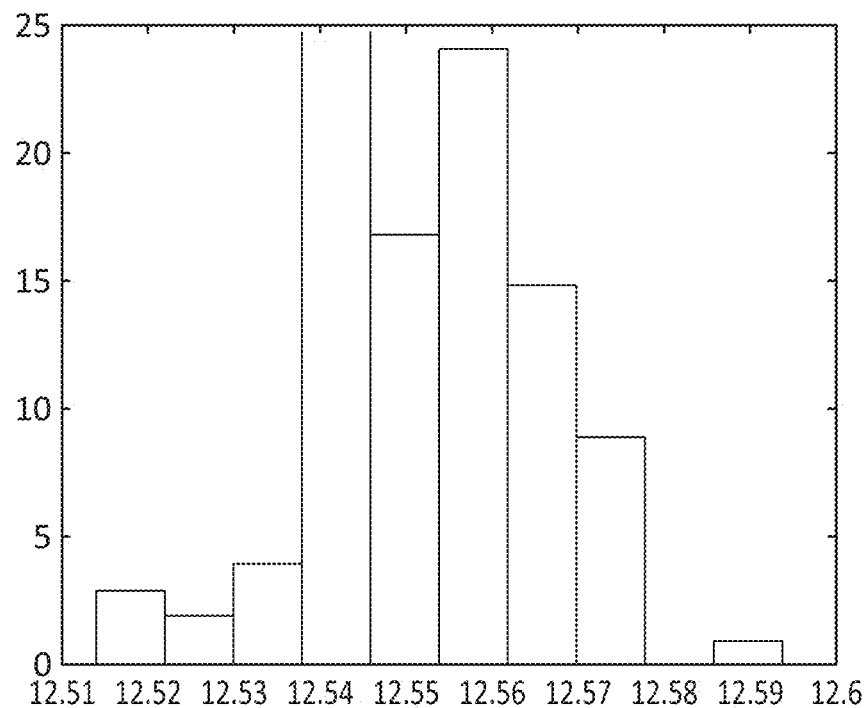

FIGS. 8A to 8D are, respectively, a photographic image and 3D-reconstruction of an actual subject's eye (i.e., not a model) utilized in testing an example embodiment of a system for measuring IOP. Results of the 3D-reconstruction are further shown in FIGS. 8E and 8F, which comprise a ten parameter pseudo-ellipsoid surface fit generated from the captured image of the subject's sclera. The pseudo-ellipsoid surface comprised over 2,000 points with a standard deviation of less than 30 um for high quality points. It is further surmised that the error is lower due to an assumption that the surface is not a perfect representation. Based on the 3D-reconstruction, a curvature integration over the fit surface was performed by bootstrapping data at a 50% subsampling rate and iteratively refitting the surface. As can be seen in the results in the graphs depicted in FIGS. 8G and 8H, the mean radius from the integrated curvature was determined to be 12.55 mm with a 0.037 standard deviation.

Figure 9A:
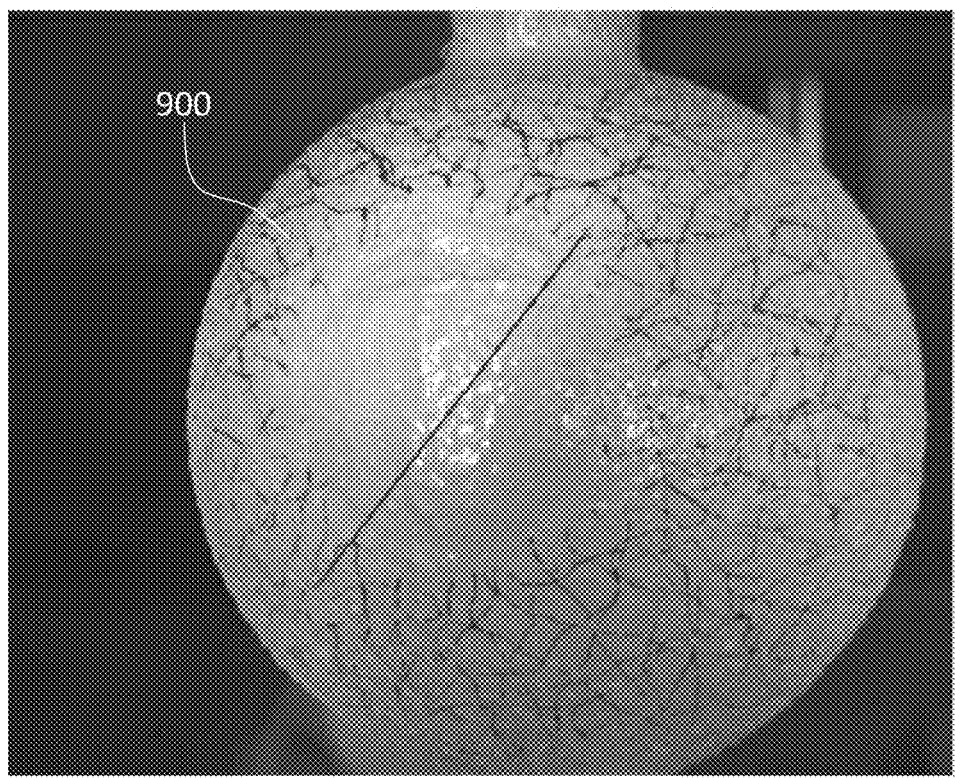
FIG. 9A is a photograph of a model used for testing an example embodiment of a system for measuring ocular properties.
Figure 9B:
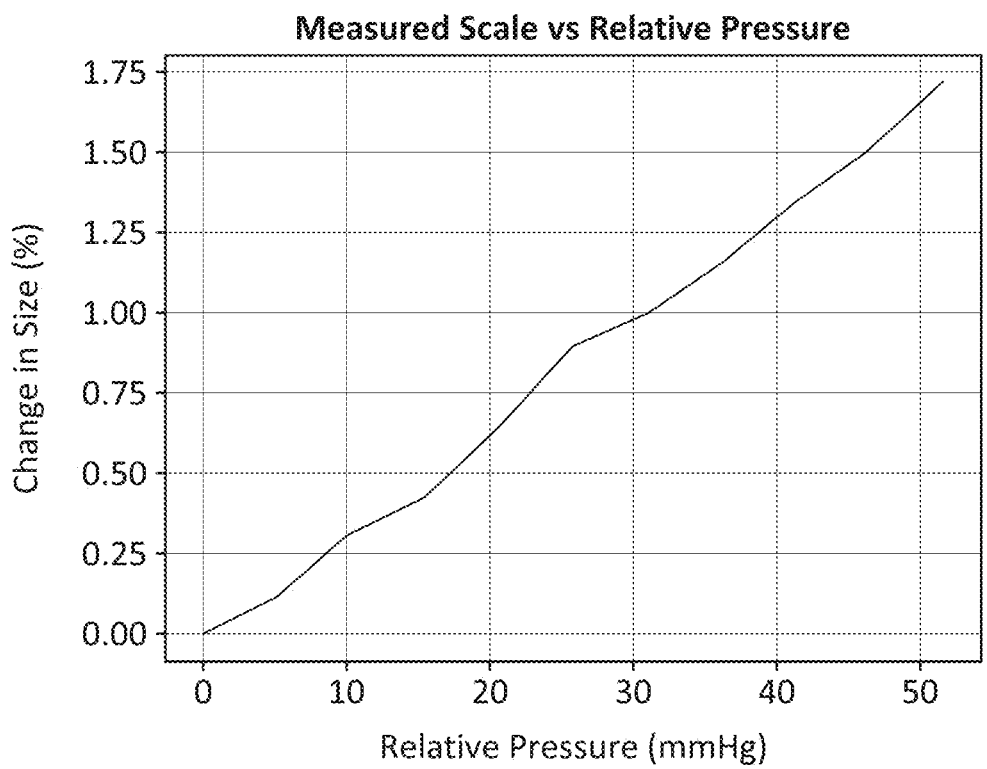
FIGS. 9B and 9C are graphs depicting measured scale versus relative pressure as determined during testing of an example embodiment of a system for measuring ocular properties.
Figure 9C:
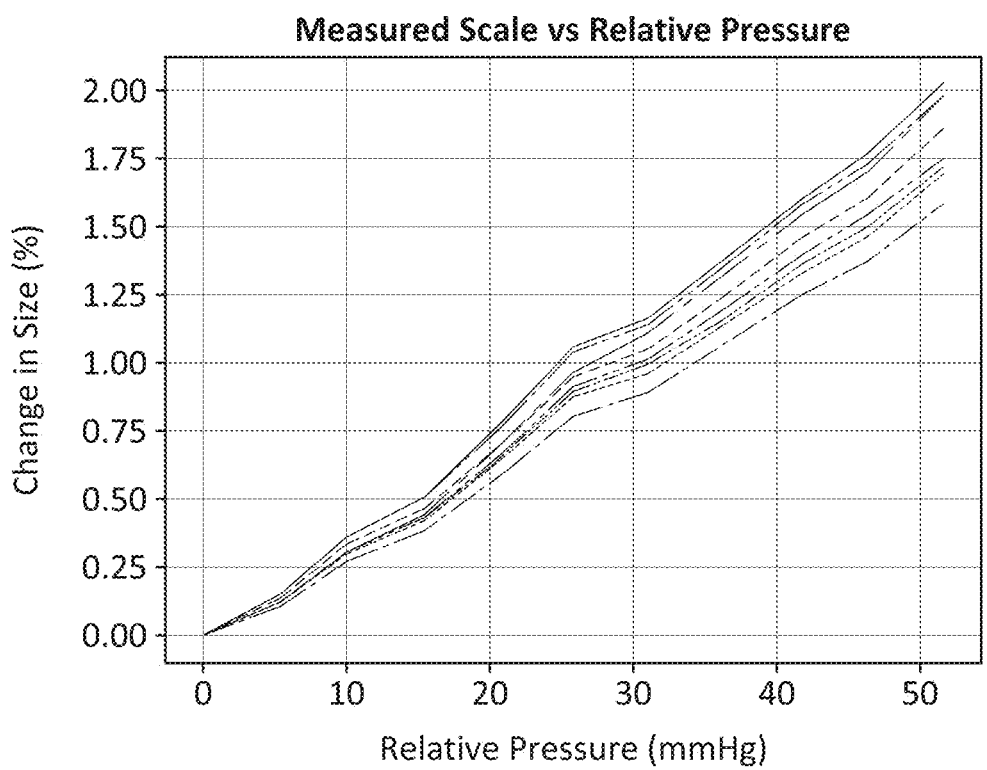

FIG. 9A is a photograph of another inflatable model 900 utilized in testing measurements of surface deformations by an example embodiment of a system for measuring IOP. According to one aspect of the experiment, model 900 was connected to a regulated air pressure system and run at the lowest possible increments. Deformation measurement results can be seen in the graph depicted in FIG. 9B, which shows that tracking corresponds to accuracies of better than 10 um per 12 mm. Surface changes were measured at approximately 0.32 um/mmHG per mm. It was determined that a uniform sphere of the tested material having a 12 mm radius would change at 3.8 um/mmHG. It was further noted that elasticity of the eye is substantially larger (e.g., 20 um/mmHG). FIG. 9C is a graph depicting measured scale versus relative pressure for multiple points being tracked on the model. According to an aspect of the experiment, the material and shape used for the model was non-uniform, and thus it was surmised that deformations would not be homogeneous. As can be seen in the graph depicted in FIG. 9C, different tracked points show strong consistency in relative scale differences. From the results, it was concluded that the example embodiment of the system for measuring IOP would be capable of working with non-uniform surface deformations.

Curvature and Volumetric Measurement

Figure 10:
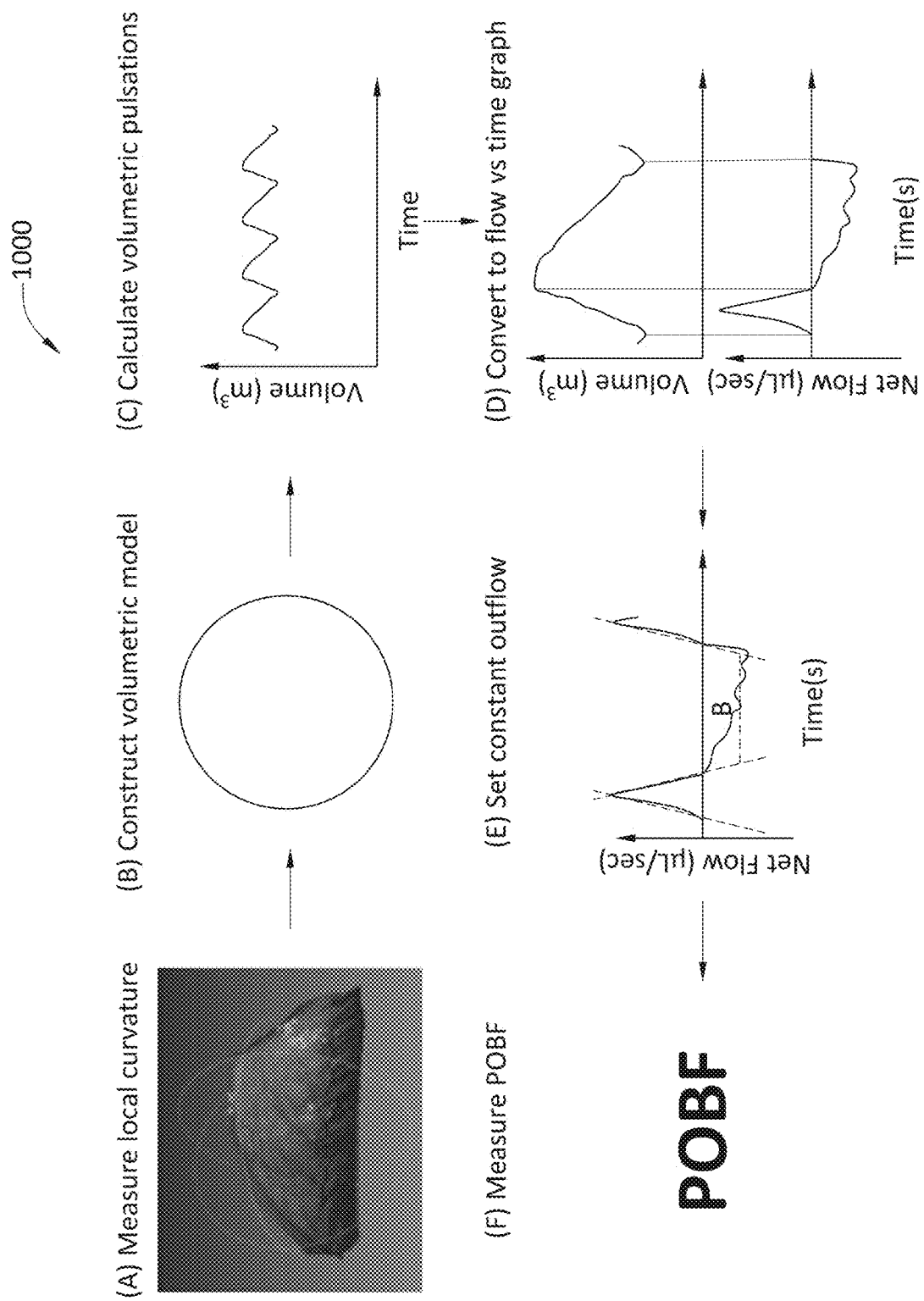
FIG. 10 pictorially illustrates a process for measuring pulsatile ocular blood flow in accordance with example embodiments of the present disclosure.

FIG. 10 illustrates a process 1000 for measuring POBF in accordance with some embodiments of the present disclosure. At the sub-process shown in FIG. 10A, the local curvature and volume of the eye over time is measured and tracked based at least on images having depth information, which are captured using high-speed imaging system 102 (see FIG. 1). The captured images can be used to generate a 3D model of the eye. In some embodiments, local curvature and volume metric measurement scan be obtained by analyzing the 3D model at a single time point and/or over multiple time points (see FIG. 10B).

For example, imaging system 102 can focus on certain portion of the eye to measure the local curvature variation with time for each ocular pressure pulse wave. The measured local curvature would then be used to reconstruct the volumetric structure of the eye at every instance of the recording (FIG. 10B). To reconstruct the volumetric structure multiple methodologies can be used. The volumetric pulsations can then be directly used to measure the net flow profile during the pulse. The constant outflow behavior of the eye can be approximated by analyzing the information in multiple pulses. With the assumption of the constant outflow, the POBF can be reconstructed for each individual pulse. To reconstruct the pulse with enough detail, it is clinically recommended to sample at a frequency of at least one hundred hertz.

At the sub-process shown in FIG. 10C, a volumetric pulsation is calculated by observing the changes in volume of one or more regions of the eye (e.g., blood vessel region) over a period of time. At the sub-process shown in FIG. 10D, the volumetric measurement is converted to a flow measurement, which can be used to estimate the total amount of fluid that enters the eye in a given period of time. In FIG. 10E, single pulse is mathematically analyzed. Given the nature of the pulsation, a convenient reference frame is marked from the start of the volumetric expansions. A single pulse would consequently terminate at the beginning of the new volumetric expansion. This definition is of particular importance when analyzing individual pulses for POBF.

In some embodiments, the pulsatile ocular blood flow can be measured by assuming a constant volume over time. Alternatively, the IOP can be measured from the ocular pulsation (see FIG. 4B). Next, the constant outflow can be calculated using the measured IOP and a constant volume over time assumption. Finally, the pulsatile ocular blood flow can be determined based on the constant outflow calculation.

It should be noted that ocular volumetric pulsations are a measurable outcome of fluid-solid interactions in the eye. With the application of machine learning applied to the measured curvature signal, further insight about ocular health can be obtained. Additional parameters not limited to POBF can be extracted from ocular local curvature variation over time. For diagnostic purposes, applying machine learning trend recognition and categorization on multiple measurable parameters can lead to a more favorable prognosis. To this end, process 1000 can be applied to any of the following but is not limited to: diabetic retinopathy, age related macular degeneration, carotid artery stenosis, and arrythmias.

Example Embodiment of Local Computing Device

Figure 11:
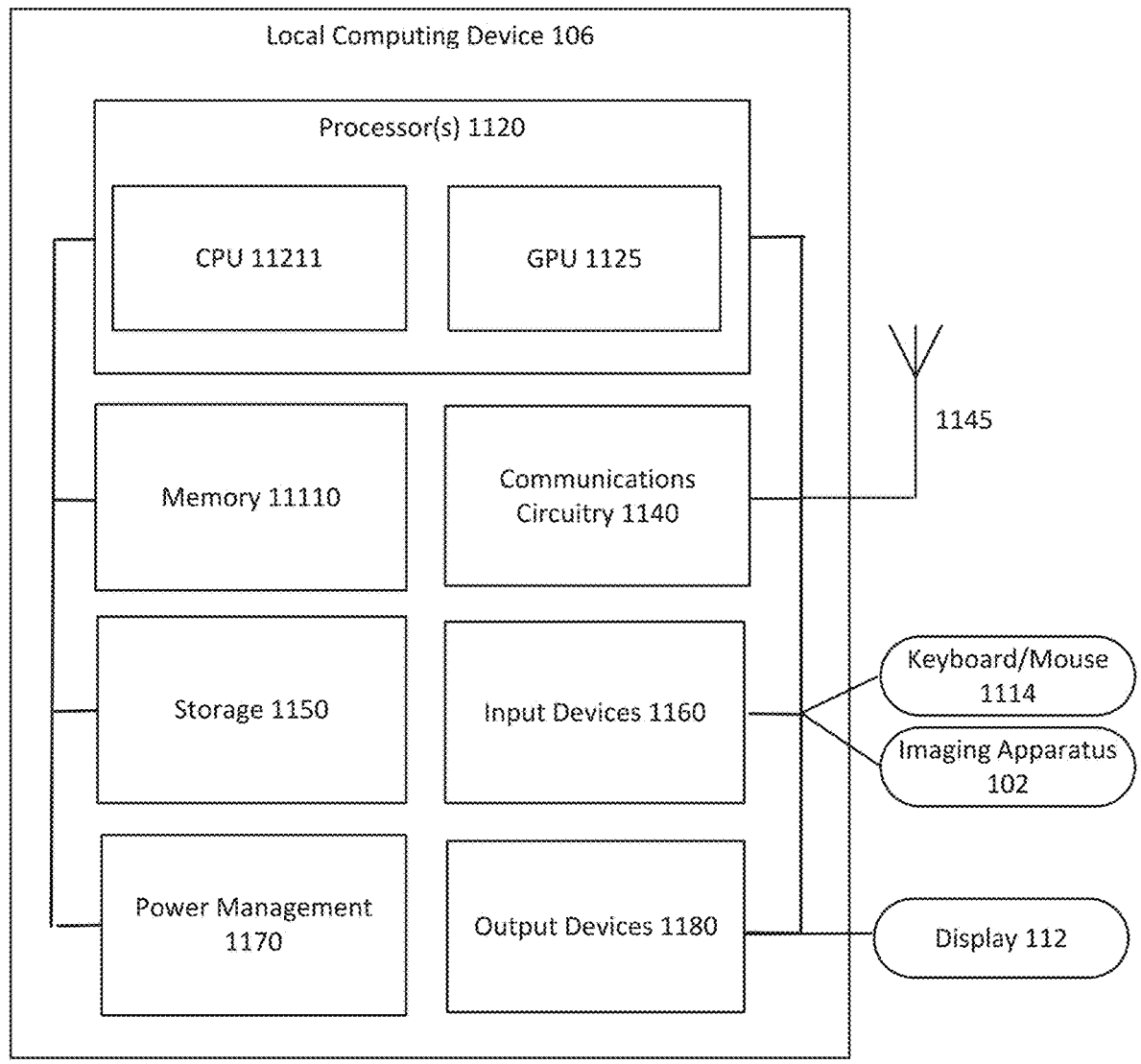
FIG. 11 is a block diagram depicting an example embodiment of a computing device for use in a system for measuring ocular properties.

FIG. 11 is a block diagram depicting an example embodiment of local computing device 106, which can include one or more processors 1120 coupled to memory 1130, communications circuitry 1140, storage device 1150, input devices 1160, power management module 1170, and output devices 1180. Processors 1120 can include, for example, a general-purpose central processing unit ("CPU") 1123, a graphics processing unit ("GPU") 1125, an application-specific integrated circuit ("ASIC"), a field programmable gate array ("FPGA"), or any other type of processor, e.g., Application-specific Standard Products ("ASSPs"), Systems-on-a-Chip ("SOCs"), Programmable Logic Devices ("PLDs"), and other similar components. Processors 1120 can include one or more processors, microprocessors, controllers, and/or microcontrollers, each of which can be a discrete chip or distributed amongst (and a portion of) a number of different chips, and collectively, can have the majority of the processing capability for executing instructions stored in memory 1130.

Memory 1130 can include volatile memory, including, e.g., high-speed random access memory such as DRAM, SRAM, DDR RAM, and/or non-volatile memory, e.g., ROM, EEPROM, flash memory, or a combination thereof that is accessible by the one or more processors 1120. Memory 1130 can be used to store instructions, for example, comprising software to implement the steps of the embodied methods disclosed herein. Similarly, storage device 1150 can include computer readable storage medium for storing instructions comprising software to implement the steps of the embodied methods disclosed herein. For example, storage device 1150 can include one or more of magnetic disk storage devices (e.g., hard disk drives ("HDDs")), optical disk storage devices, Blu-Ray BD-ROMs, DVDs, CD-ROMs, flash memory devices or other non-volatile solid-state storage devices.

Referring still to FIG. 11, communications circuitry 1140 can include any transceiver-like mechanism that enables local computing device 106 to communicate with other devices and/or systems through an electrical, optical, RF or other carrier medium. Communications circuitry 1140 can also include either or both wireless and wired network interfaces. In some embodiments, for example, communications circuitry 1140 can include one or more ethernet ports, an 802.11x wireless network (also referred to as "Wi-Fi X") port, and a Bluetooth or Bluetooth Low Energy ("BLE") wireless link port capable of supporting multiple Bluetooth and/or BLE connections. As can be seen in FIG. 11, communications circuitry 1140 can also be coupled to an antenna 1145.

According to another aspect of the disclosed embodiments, local computer device 106 can also include a power management module 1170 for managing and conserving power for the various components of local computing device 106; output devices 1180 including display 112, projectors, printers and speakers (not shown); as well as input devices 1160 including imaging apparatus 102, keyboards and/or mice 1114, trackpads, touchpads, touchscreens, microphones, voice recognition devices, biometric devices and any other external and/or peripheral device adapted for receiving input from a user. As understood by one of skill in the art, all of the aforementioned components are electrically and communicatively coupled in a manner to make one or more functional devices.

Example Embodiment of Remote Server

Figure 12:
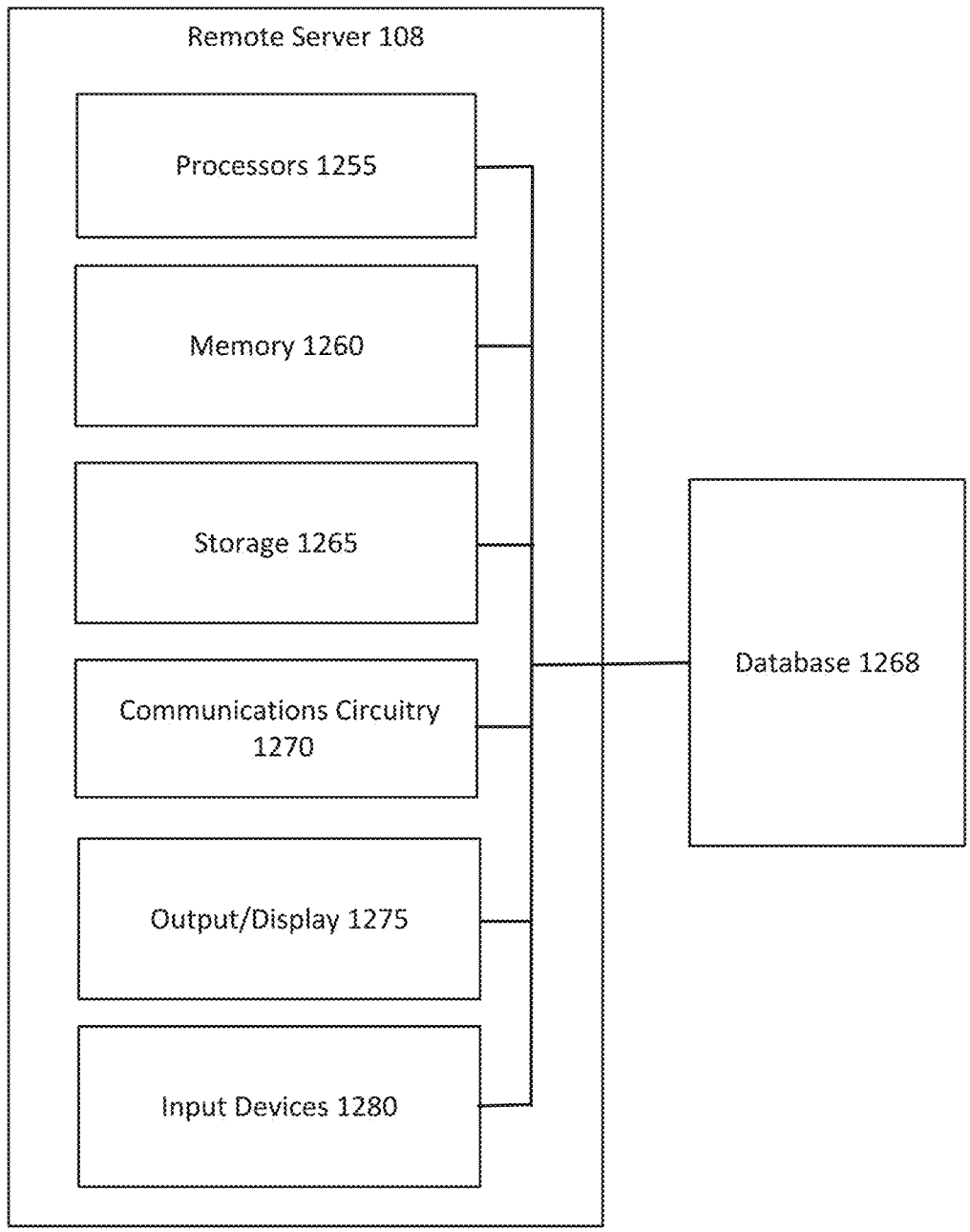
FIG. 12 is a block diagram depicting an example embodiment of a remote server for use in a system for measuring ocular properties.

FIG. 12 is a block diagram depicting an example embodiment of remote server 108. As shown in the diagram, remote server 108 can include an output/display component 1275, one or more processors 1255, memory 1260, including non-transitory memory, RAM, Flash or other types of memory, communications circuitry 1270, which can include both wireless and wired network interfaces, mass storage devices 1265, and input devices 1280, which can include keyboards, mice, trackpads, touchpads, microphones, and other user input devices. The one or more processors 1255 can include, for example, a general-purpose CPU, a GPU, an ASIC, an FPGA, ASSPs, SOCs, PLDs, and other similar components, and furthermore, can comprise one or more processors, microprocessors, controllers, and/or microcontrollers, each of which can be a discrete chip or distributed amongst (and a portion of) a number of different chips. As understood by one of skill in the art, these components are electrically and communicatively coupled in a manner to make a functional device.

Referring still to FIG. 12, remote server 108 can include database 1268 for storing image data or processed image data received from local computing device 106, imaging apparatus 102, and/or mobile computing device 110. In some embodiments, database 1268 can be part of a storage area network, for example, to which remote server 108 is communicatively coupled. In many embodiments, communications circuitry 1270 can include a single network interface, either wired or wireless; or, in other embodiments, communications circuitry 1270 can include multiple network interfaces, either wired or wireless, to provide for enhanced security, monitoring and traffic shaping and management.

Example Embodiment of Mobile Computing Device

Figure 13:
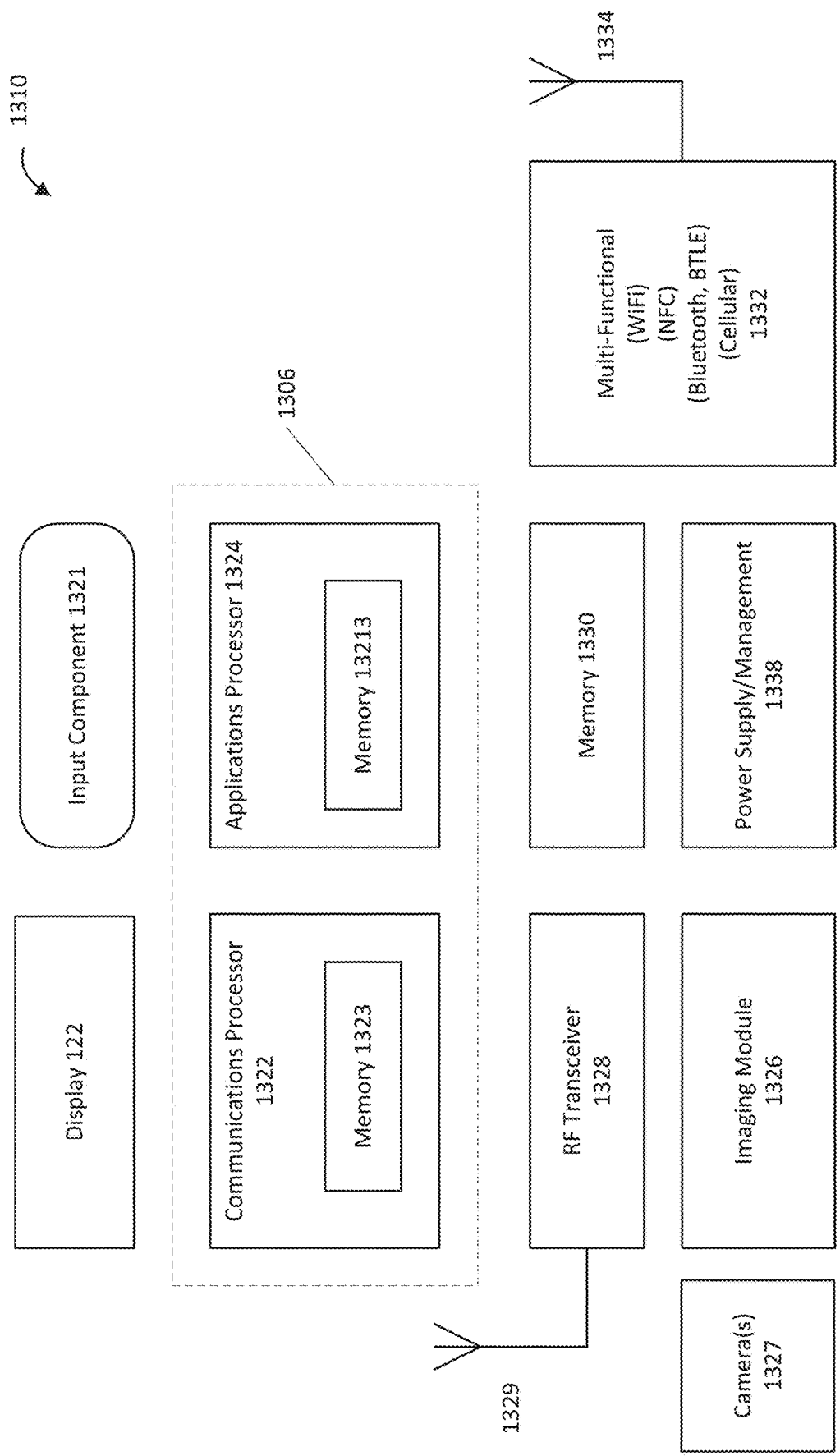
FIG. 13 is a block diagram depicting an example embodiment of a mobile computing device for use in a system for measuring ocular properties.

FIG. 13 is a block diagram depicting an example embodiment of a mobile computing device 120, which can be, e.g., a smartphone, PDA, or tablet device. Mobile computing device 120 includes an imaging module 1326 coupled to one or more cameras 1327, wherein imaging module 1326 is configured to cause the one or more cameras 1327 to capture a digital image of the patient's eye. Additionally, mobile computing device 120 can include a display 122, input component 1321, and a processing core 1306 including a communications processor 1322 coupled with memory 1323 and an applications processor 1324 coupled with memory 1325. Also included can be separate memory 1330, RF transceiver 1328 with antenna 1329, and power supply and power management module 1338. Further, mobile computing device 120 can also include a multi-functional transceiver 1332 which can communicate over Wi-Fi, NFC, Bluetooth, BTLE, and cellular networks with an antenna 1334. As understood by one of skill in the art, these components are electrically and communicatively coupled in a manner to make a functional device.

ADDITIONAL EMBODIMENTS

In many embodiments, a system for measuring intraocular pressure of a patient's eye is disclosed. The system can include an imaging apparatus configured to capture three-dimensional (3D) images of a sclera of the patient's eye; one or more processors communicatively coupled with the imaging apparatus; and non-transitory memory coupled to the one or more processors. The non-transitory memory can store instructions that, when executed by the one or more processors, cause the one or more processors to: cause the imaging apparatus to capture a first set of 3D images of the sclera, receive a reference IOP measurement and a plurality of blood pressure measurements synchronously taken with the first set of 3D images, wherein the plurality of blood pressure measurement includes a first blood pressure value and a second blood pressure value, generate a first 3D image 3D-reconstruction of the sclera based on the first set of 3D images, identify blood vessel patterns (BVPs) in the first 3D image 3D-reconstruction and extract a first set of curvature metrics of the sclera, determine a first deformation value between the first blood pressure value and the second blood pressure value, and determine a rate-of-linear-change to IOP-change relationship based on the reference IOP measurement, the first deformation value, and the first set of curvature metrics. The instructions can further include instructions, when executed by the one or more processors, further cause the one or more processors to: cause the imaging apparatus to capture a second set of 3D images of the sclera, generate a second 3D image reconstruction of the sclera based on the second set of 3D images, identify the BVPs in the second 3D image reconstruction and extract a second set of curvature metrics of the sclera, determine a second deformation value based on a comparison of the BVPs in the first and the second 3D image reconstruction, and determine an intraocular pressure measurement based on the second deformation and the rate-of-linear-change to IOP-change relationship.

The system can display the output the intraocular pressure measurement on a display. The intraocular pressure measurement can be measured as a change in intraocular pressure. The reference IOP measurement is taken by a standard ocular tonometry of the patient's eye without using pressure-modifying eye drops.

The imaging apparatus can have two or more cameras in a stereoscopic alignment. The imaging apparatus can also have a telecentric lens with a second off-axis camera. The imaging apparatus can include a defocusing system with two or more apertures. Additionally, the imaging apparatus can include one or more off-axis cameras having Scheimpflug angles configured to give aligned focal planes. The imaging apparatus can also include folded optics and/or custom optics made to match an eye curvature of a focal plane. The imaging apparatus can further include an f-theta lens. The imaging apparatus can also include a light source that generates light at a wavelength between 350 nm and 450 nm. The light source can include one or more of a light-emitting diode (LED), a laser, and a filtered broadband light source. The imaging apparatus is configured to capture video of the sclera at a rate greater than 30 Hz.

In some embodiments, the instructions to determine the first and the second deformation values include measuring distances of areas between BVPs and/or measuring distances between point pairs of similar elevation.

The first blood pressure value can be a diastolic blood pressure value and the second blood pressure value can be a systolic blood pressure value.

The instructions, when executed by the one or more processors, can further cause the one or more processors to: combine the intraocular pressure measurement with one or more physiological measurements, and generate a medical diagnosis based on the combined intraocular pressure measurement and the one or more physiological measurements.

The instructions, when executed by the one or more processors, can further cause the one or more processors to encrypt and store in the non-transitory memory acquired data that can include one or more of: the first and the second sets of 3D images, the reference IOP measurement, the plurality of blood pressure measurements, the first and the second 3D image reconstructions, the first and the second set of curvature metrics, the first and the second deformation values, the rate-of-linear-change to IOP-change relationship, or the intraocular pressure measurement.

It should be noted that in any of the aforementioned processes (e.g., processes 500, 600, 630, 660, 690), any of the sub-processes or steps can be performed out of order or be omitted entirely. Additionally, any of the sub-processes can be performed automatically and/or be combined with one or more other sub-processes.

Throughout this disclosure, the preferred embodiment and examples illustrated should be considered as exemplars, rather than as limitations on the present inventive subject matter, which includes many inventions. As used herein, the term "inventive subject matter," "system," "device," "apparatus," "method," "present system," "present device," "present apparatus" or "present method" refers to any and all of the embodiments described herein, and any equivalents.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

When an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the inventive subject matter. As used herein, the term "and/or" includes any and all combinations of one or more of the associated list items.

The terminology used herein is for the purpose of describing particular embodiments only and is not intended to be limiting. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It will be further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments are described herein with reference to view illustrations that are schematic illustrations. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region and are not intended to limit the scope of the inventive subject matter.

The foregoing is intended to cover all modifications, equivalents and alternative constructions falling within the spirit and scope of the invention as expressed in the appended claims, wherein no portion of the disclosure is intended, expressly or implicitly, to be dedicated to the public domain if not set forth in the claims. Furthermore, any features, functions, steps, or elements of the embodiments may be recited in or added to the claims, as well as negative limitations that define the inventive scope of the claims by features, functions, steps, or elements that are not within that scope.

What is claimed is:

1. A system for performing contactless measurement of one or more characteristics of a patient's eye used to diagnosis a potential medical condition, the system comprising:
   a light source configured to illuminate the eye;
   a 3D-camera assembly configured to capture a plurality of images of the eye, wherein the plurality of images comprises depth information;
   a 3D-reconstruction module configured to generate a 3D model of a portion of the eye based at least on the plurality of images; and
   a data analytic module configured to determine one or more characteristics of the eye based at least on the 3D model.

2. The system of claim 1, wherein the one or more characteristics of the eye comprises one or more of blood vessel features, curvature metrics of a sclera of the eye, volumetric pulsations of the eye, total eye volume, deformations, relative local displacements over time, rate of local blood outflow, and radius of the eye.

3. The system of claim 2, further comprising an intraocular pressure (TOP) diagnostic module configured to determine the TOP within the eye based at least on the rate of local blood outflow.

4. The system of claim 3, further comprising a blood pressure measuring apparatus configured to synchronously measure the patient's blood pressure, and wherein the TOP diagnostic module is configured to determine the TOP within the eye based at least on the patient's blood pressure and the rate of local blood outflow.

5. The system of claim 2, further comprising:
   a heart monitor configured to obtain heart data of the patient's heart; and
   a diagnostic module configured to flag a potential medical condition based at least on (a) deformations of the eye and the heart data, (b) relative local displacements over time and heart data, OR (c) variation in the relative local displacements over time and heart data.

6. The system of claim 2, further comprising a diagnostic module configured to determine pulsatile ocular blood flow (POBF) based at least on the volumetric pulsations of the eye.

7. The system of claim 1, wherein the 3D-camera assembly comprises a plurality of cameras in stereoscopic alignment or a camera configured to capture a plurality of images at different focuses.

8. The system of claim 1, wherein the 3D-camera assembly comprises a telecentric camera and an off-axis camera or one or more off-axis cameras with Scheimpflug angles.

9. The system of claim 1, wherein the 3D-camera assembly comprises a light-based imaging system.

10. The system of claim 9, wherein the light-based imaging system comprises one of a RGB-D camera, a light ranging and detection (LIDAR) system, a structured light system, or a time of flight system.

11. The system of claim 1, wherein the 3D-camera assembly comprises one or more high-speed cameras configured to capture images at a frame rate between 30-5000 frames per second.

12. The system of claim 1, wherein the light source comprises a wavelength having a range between 350 and 450 nm.

13. The system of claim 12, wherein the light source comprises a wavelength having a range of 395 to 405 nm.

14. A system for identifying potential medical conditions using contactless measurement of one or more characteristics of a patient's eye, the system comprising:
   a light source configured to illuminate the eye;
   an image capturing assembly configured to capture a plurality of images of the eye, wherein the plurality of images comprises depth information;
   a non-transitory memory configured to store instructions that, when executed by one or more processors, cause the one or more processors to:
      generate a 3D model of a portion of the eye based at least on the plurality of images;
      determine one or more characteristics of the eye based at least on the 3D information, wherein the one or more characteristics comprise one or more of blood vessel features, curvature metrics of a sclera of the eye, volumetric pulsations of the eye, total eye volume, deformations, relative local displacements over time, and radius of the eye; and
      identify a potential medical condition based at least on the one or more characteristics of the eye.

15. The system of claim 14, wherein the image capturing assembly comprises one or more high-speed cameras configured to capture images at a frame rate between 30-5000 frames per second or a light-based camera system.

16. The system of claim 14, wherein the light source comprises a wavelength having a range between 350 and 450 nm.

\* \* \* \* \*